(12) United States Patent
Kemmer et al.

(10) Patent No.: US 8,506,950 B2
(45) Date of Patent: Aug. 13, 2013

(54) DEGRADABLE MICROCAPSULES

(75) Inventors: Christian Kemmer, Riehen (CH);
David Fluri, Zürich (CH); Ulrich Witschi, Liebefeld (CH); Wilfried Weber, Freiburg im Breisgau (DE);
Martin Fussenegger, Mägenwil (CH)

(73) Assignees: ETH Zurich, Zurich (CH);
Swissgenetics, Zollikofen (CH)

( * ) Notice: Subject to any disclaimer, the term of this patent is extended or adjusted under 35 U.S.C. 154(b) by 0 days.

(21) Appl. No.: 13/605,307

(22) Filed: Sep. 6, 2012

(65) Prior Publication Data

US 2013/0045190 A1    Feb. 21, 2013

Related U.S. Application Data

(62) Division of application No. 13/003,420, filed as application No. PCT/EP2009/058792 on Jul. 10, 2009, now Pat. No. 8,388,945.

(30) Foreign Application Priority Data

Jul. 11, 2008 (EP) .................................. 08104713

(51) Int. Cl.
*A61K 35/12* (2006.01)
*A61P 15/00* (2006.01)
*C12N 5/00* (2006.01)

(52) U.S. Cl.
USPC ........................................ 424/93.21; 435/325

(58) Field of Classification Search
USPC ........................................ 424/93.21; 435/325
See application file for complete search history.

(56) References Cited

U.S. PATENT DOCUMENTS

| 5,952,020 | A | 9/1999 | Lizak |
| 2005/0281781 | A1 | 12/2005 | Ostroff |

FOREIGN PATENT DOCUMENTS

| WO | 02/057436 | 7/2002 |
| WO | 02/058735 | 8/2002 |
| WO | 03/025184 | 3/2003 |
| WO | 2004/094619 | 11/2004 |
| WO | 2005/023096 | 3/2005 |
| WO | 2009-058913 | 5/2009 |

OTHER PUBLICATIONS

International Search Report issued Aug. 3, 2010 in International (PCT) Application No. PCT/EP2009/058792 along with the Written Opinion.
W. Weber et al., "Design of high-throughput-compatible protocols for microencapsulation, cryopreservation and release of bovine spermatozoa", Journal of Biotechnology, vol. 123, No. 2, pp. 155-163, May 17, 2006.
W. Weber et al., "CellMAC: a novel technology for encapsulation of mammalian cells in cellulose sulfate/pDADMAC capsules assemble on a transient alginate/$Ca^{2+}$ scaffold", Journal of Biotechnology, vol. 114, No. 3, pp. 315-326, Nov. 9, 2004.
W. Weber et al., "Macrolide-based transgene control in mammalian cells and mice", Nature Biotechnology, vol. 20, No. 9, pp. 901-907, Sep. 1, 2002.
J. M. Rabanel et al., "Progress Technology in microencapsulation methods for cell therapy", Biotechnology Progress, vol. 25, No. 4, pp. 946-963, Jul. 2009.
D. A. Fluri et al., "A novel system for trigger-controlled drug release from polymer capsules", Journal of Controlled Release, vol. 131, No. 3, pp. 211-219, Nov. 12, 2008.

*Primary Examiner* — Marcia S Noble
(74) *Attorney, Agent, or Firm* — Wenderoth, Lind & Ponack, L.L.P.

(57) ABSTRACT

The invention relates to microcapsules consisting of a polymer degradable by a polypeptide comprising a drug or other compound of interest and a genetically engineered cell expressing said polypeptide in response to a triggering compound, and to methods of directed release of the compound of interest. The preferred polymer is optionally modified cellulose sulfate/poly-diallyl-dimethyl-ammonium chloride. Such microcapsules are non-toxic, do not elicit an immunological response and have an extended half-life time in mammals. The expression system for cellulase is, for example, based on TET and doxycycline, or E.REX and erythromycin. In another example, expression of cellulase is triggered by luteinizing hormone, which can be used for artificial insemination with microcapsules carrying sperm.

12 Claims, 14 Drawing Sheets

DEGRADABLE MICROCAPSULES

This application is a Divisional of U.S. application Ser. No. 13/003,420, filed Jan. 10, 2011 now U.S. Pat. No. 8,388,945, which is a U.S. national stage of International Application No. PCT/EP2009/058792 filed Jul. 10, 2009.

FIELD OF THE INVENTION

The invention relates to microcapsules consisting of a polymer degradable by a polypeptide, the microcapsules comprising a drug or other compound of interest and a genetically engineered cell expressing the polypeptide in response to a triggering compound, and to methods of directed release of the compound of interest.

BACKGROUND OF THE INVENTION

The controlled release of bioactive molecules from polymer matrices or polymer capsules has been proposed as a promising approach in various therapeutic interventions in order to avoid multiple dosing and to sustain continuous or pulsed release over time. The entrapment and immuno-isolation of small-molecule drugs, hormones, protein therapeutics or cell lines engineered for production of biologics in the patient's body have been designed for the treatment of various diseases such as infections, cancer, diabetes and different genetic disorders. Most controlled release systems currently available have either been chemically designed for sustained auto-catalytic or tissue-specific discharge of the therapeutic cargo, or engineered to release the therapeutic load in response to physical cues such as pH, light, ionic strength, magnetic resonance, or an electric field. Unfortunately, polymers designed for controlled release are often limited in their chemical flexibility, while most physical stimuli are impractical for in vivo applications. Also, the timing of release and overall release kinetics are often difficult to control.

Microencapsulation of viable genetically modified cells has become a widely used technology for cell-based therapeutic strategies and biopharmaceutical manufacturing. The encapsulation in biocompatible and immuno-isolating matrices protects the cells from environmental stress while providing favourable local conditions. Additionally, nutrients, waste products and therapeutics may freely penetrate the semi-permeable membrane of capsules. The ability to implant genetically engineered cells in immuno-protective materials may have great potential for therapeutic uses. The integration of mammalian cells in varying encapsulating polymers have lead to therapeutic strategies for the treatment of cancer, diabetes, hemophilia B, ischemia heart disease and other human disorders [see e.g. Zhang Y, Wang W, Zhou J, Yu W, Zhang X, Guo X, Ma X, Ann Biomed Eng 2007; 35:605-14]. In animal models, the immuno-protection by microcapsules even allowed the transplantation of xenogenic cells without rejection of implanted cells [Schneider S, Feilen P J, Brunnenmeier F, Minnemann T, Zimmermann H, Zimmermann U, Weber M M, Diabetes 2005; 54:687-93]. Additionally, a host-independent long-term drug delivery method by encapsulated cells has been reported in a mouse disease model [Orive G, de Castro M, Ponce S, Hernandez R M, Gascon A R, Bosch M, Alberch J, Pedraz J L, Mol Ther 2005; 12:283-9].

In the last three decades various materials were tested for their potential immuno-protection and biocompatibility properties. Sodium alginate, a natural polymer isolated from brown algae, which is able to precipitate in the presence of poly-L-lysine (PLL) was widely used for the production of microcapsules. However, the low quality reliability and poor biocompatibility of the precipitation agent PLL resulted in its replacement by other materials. In various studies sodium cellulose sulfate (CS)/poly-diallyl-dimethyl-ammonium chloride (pDADMAC) capsules showed less immunogenicity and higher biocompatibility than alginate/PLL. Furthermore, CS/pDADMAC capsules can be produced in a one-step high throughput procedure [Weber W, Rimann M, Schafroth T, Witschi U, Fussenegger M, J Biotechnol 2006; 123:155-63]. A clinical phase I/II long-term study demonstrated that CS/pDADMAC encapsulated cells showed no foreign body reaction or alteration of the recipient immune system and that cells may survive for a nearly unlimited time span [Gunzburg W, Salmons B, Trends Mol Med 2001; 7:30-7]. CS/pDADMAC encapsulated cells can be also successfully frozen and retain viability after thawing. Cellulases, which can cleave the polymer backbone of CS/pDADMAC capsules, are typically absent from mammalian tissues.

TET [Gossen M, Bujard H, Proceedings of the National Academy of Sciences USA 1992; 89(12):5547-51] or E.REX [Weber W, Fux C, Daoud-el Baba M, Keller B, Weber C C, Kramer B P, Heinzen C, Aubel D, Bailey J E, Fussenegger M, Nature biotechnology 2002; 20(9):901-7] are systems for trigger-inducible expression and secretion by mammalian cells. TET/E.REX are prototypic transgene control system which are responsive to clinically licensed antibiotics (tetracycline/doxycycline, erythromycin) and consist of chimeric transactivators designed by fusing bacterial response regulators to a eukaryotic transactivation domain, which binds and activates promoters containing transactivator-specific operator sites 5' of minimal eukaryotic promoters. In the presence of regulating antibiotics the transactivators are released from their cognate promoters and transgene expression is silenced in a dose-dependent manner [Weber W, Fussenegger M, Current opinion in biotechnology 2007; 18(5):399-410; Weber W, Fussenegger M, The journal of gene medicine 2006; 8(5): 535-56].

Artificial insemination (AI) of cattle is the major reproduction technology used in modern stock farming. In northern and western European countries the artificial inseminated reproduction of diary cattle exceeds 95%. The success of AI is strongly dependent on a precise determination of ovulation and a temporally coordinated insemination. The efficiency of AI is limited by the sperm survival in utero, which is compromised by leucocyte mediated phagocytosis and sperm retrograde transport, limiting the fertilization period to approximately 20 hours. As a result, the rate of successful artificially inseminated cows (non-return rate) does not exceed 70%. The ovulation in mammalian is a complex and primarily hormone-controlled process that plays a critical role in reproductive physiology. Initiation of ovulation is stimulated by a strong and highly specific preovulatory surge of the pituitary luteinizing hormone (LH). The LH binds to the luteinizing hormone receptor (LHR) that is expressed on the granulosa and theca cells of the mature preovulatory ovarian follicle. Upon activation the LHR couples to numerous G-proteins resulting in the stimulation of the cyclic adenosine monophosphate (cAMP) and inositol-phosphate signaling cascades followed by reprogramming of the cells. The luteinization of the granulosa and theca cells leads to a rupture of the mature follicle and a release of the fertilizable oocyte.

SUMMARY OF THE INVENTION

The invention relates to a semipermeable microcapsule consisting of a polymer degradable by a polypeptide comprising a genetically engineered cell expressing said polypeptide in response to a triggering compound, and optionally one or more compounds of interest.

In a particular embodiment the polymer is cellulose or a cellulose derivate and the polypeptide is cellulase.

The preferred polymer is cellulose sulfate/poly-diallyl-dimethyl-ammonium chloride, or cellulose sulfate modified with carboxymethyl cellulose/poly-diallyl-dimethyl-ammonium chloride. Such microcapsules are non-toxic, do not elicit an immunological response and have an extended half-life time in mammals. They are permeable for compounds with a molecular weight below 20-50 kDA.

In one embodiment, the microcapsules according to the invention comprise cells expressing cellulase wherein the expression system and corresponding triggering compound is TET and doxycycline, or E.REX and erythromycin.

In another embodiment, the microcapsule according to the invention comprise cells expressing cellulase wherein the expression system and corresponding triggering compound is luteinizing hormone receptor, preferably rat luteinizing hormone receptor, and luteinizing hormone.

Such microcapsules are useful to carry therapeutic compounds to be set free on adding a triggering compound activating expression of the polypeptide, for example cellulase in one of the preferred embodiments. The compound of interest may also be expressed and secreted by an encapsulated genetically engineered cell responding to the same or a different triggering compound, e.g. an endogenous hormone or signalling compound.

The invention further relates to a method of treating a disease comprising administering to a patient in need thereof a therapeutically effective amount of a microcapsule consisting of a polymer degradable by a polypeptide comprising a therapeutic drug against the disease and a cell expressing the polypeptide triggered by a signalling compound for the disease.

The invention further relates to a method of artificial insemination comprising administering to a female animal an effective amount of a microcapsule consisting of a polymer degradable by a polypeptide comprising sperm and a cell expressing the polypeptide triggered by luteinizing hormone, and optionally another cell expressing annexins, preferably annexin 1 or 5, to promote binding and prolong the survival time of sperm.

(A) Schematic representation of vectors used.

(B) Transient expression of cellulase in HEK293-T, HeLa, HT-1080, BHK-21 and CHO-K1 cells. Cellulase was either driven by a constitutive ($P_{hCMV}$) or antibiotic-responsive promoters ($P_{hCMV*-1}$ and $P_{ETR}$).

(C) Western blot analysis of cell culture supernatants derived from HEK293-T populations transiently transfected with (i) pDF196 and cultivated in the presence or absence of the glycosylation inhibitor tunicamycin (2 μg/ml), (ii) pDF301/pSAM200 (+/−DOX [2 μg/ml]) or (iii) mock-transfected to provide a negative control.

(D) Relative cellulose activity at different incubation temperatures.

(E) Stability of cellulose incubated at 37° C. in human AB serum.

Abbreviations: C, cellulase; CA, cellulase activity; DOX, doxycycline; EM, erythromycin; ET1, erythromycin-dependent transactivator; $I_{\beta-g}$, intron β-globin; M, mock transfection; $pA_{hGH}$, polyadenylation signal of the human growth hormone; $pA_{SV40}$, polyadenylation signal of the simian virus 40; $P_{hCMV*-1}$, tetracycline-responsive promoter; $P_{ETR}$, erythromycin-responsive promoter; $P_{hCMV}$, human cytomegalovirus immediate early promoter; $P_{SV40}$, simian virus 40 promoter; RA, relative activity; $SS_{Igk}$, signal sequence derived from the murine Igκ-chain V-12-C region; T, temperature; t, time; Tu, tunicamycin; tTA, tetracycline-dependent transactivator; $T_{myc}$, protein tag encoding a c-myc epitope.

Figure 2:
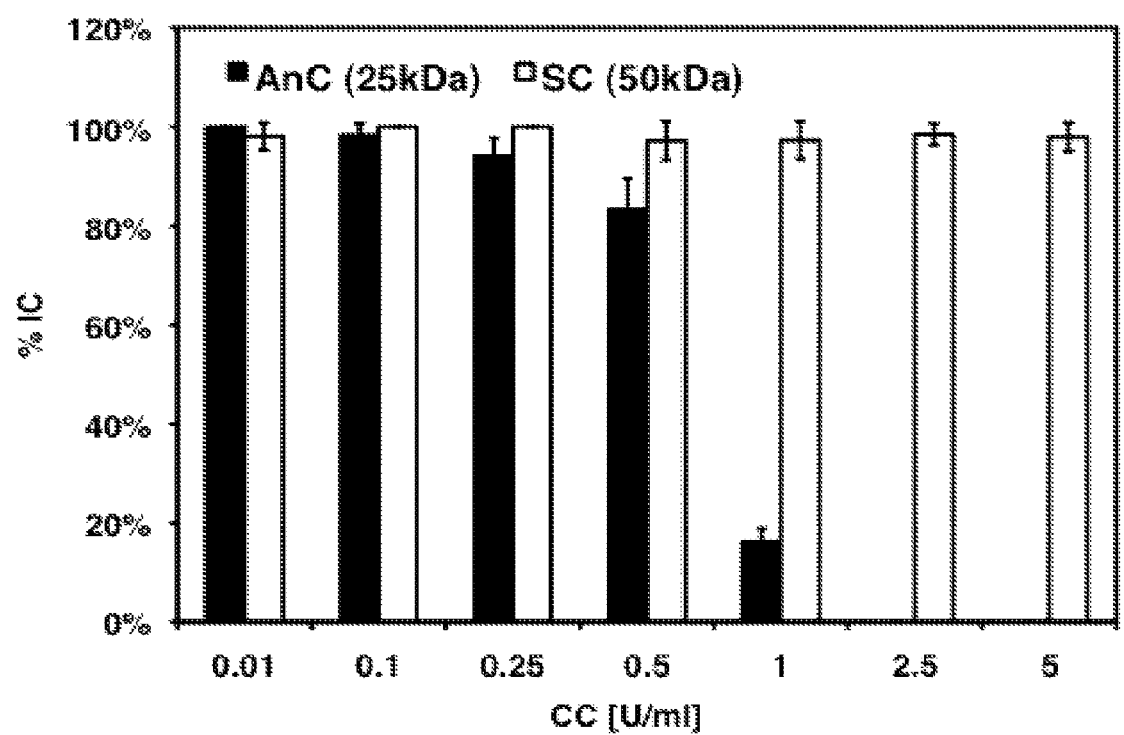

FIG. 2. Membrane properties of CS-pDADMAC capsules.

CS-pDADMAC capsules were incubated for 30 min in the presence of increasing concentrations of either a fungal cellulase (MW 25 kDa) or SecCell derived from mammalian culture supernatants (MW 50 kDa). The percentage of intact capsules was normalized to capsules, which had not been exposed to any cellulase.

Abbreviations: AnC, *A. niger* cellulase; CC, cellulase concentration; IC, intact capsules; SC, SecCell FIG. 3. Capsule rupture induced by DOX-controlled SecCell expression.

CHO-SEAP$_{18}$ were co-encapsulated with HEK-301$_9$, and capsules were cultivated in the presence (2 μg/ml) or absence of DOX for 6 days. Cumulative SEAP activity in the supernatant was measured every 24 hours. Capsule populations containing CHO-SEAP$_{18}$ together with parental HEK293-T served as a negative control.

Abbreviations: S, SEAP production; t, time.

FIG. 4. Modulation of release patterns.

(A) CHO-SEAP$_{18}$ were co-encapsulated with HEK-301$_9$ and capsule rupture was induced at different points in time (0, 24 and 48 hours) after encapsulation. Cumulative SEAP activity in the supernatant was then analyzed every 24 hours for the next 6 days and compared to readings for capsules cultivated in the presence of doxycycline (DOX) for the entire period of time.

(B) CHO-SEAP$_{18}$, co-encapsulated with HEK-301$_9$ and incubated at different DOX concentrations (♦ 20 ng/ml, ▲ 2 ng/ml, ■ 0.5 ng/ml, Δ 0.1 ng/ml and ● 0 ng/ml). SEAP accumulation in the supernatant was measured every 24 hours for 6 days.

(C) CHO-SEAP$_{18}$ was co-encapsulated with different numbers of cells ($5 \times 10^4$ cells/ml, $5 \times 10^5$ cells/ml and $1 \times 10^6$ cells/ml) of HEK-301$_9$ and incubated in the presence and absence of DOX for 6 days. Cumulative SEAP activity was measured in the supernatant every 24 hours.

Abbreviations: C, cells; NR, no release; R, release (0/24/48 h); S, SEAP production; t, time.

Figure 5:
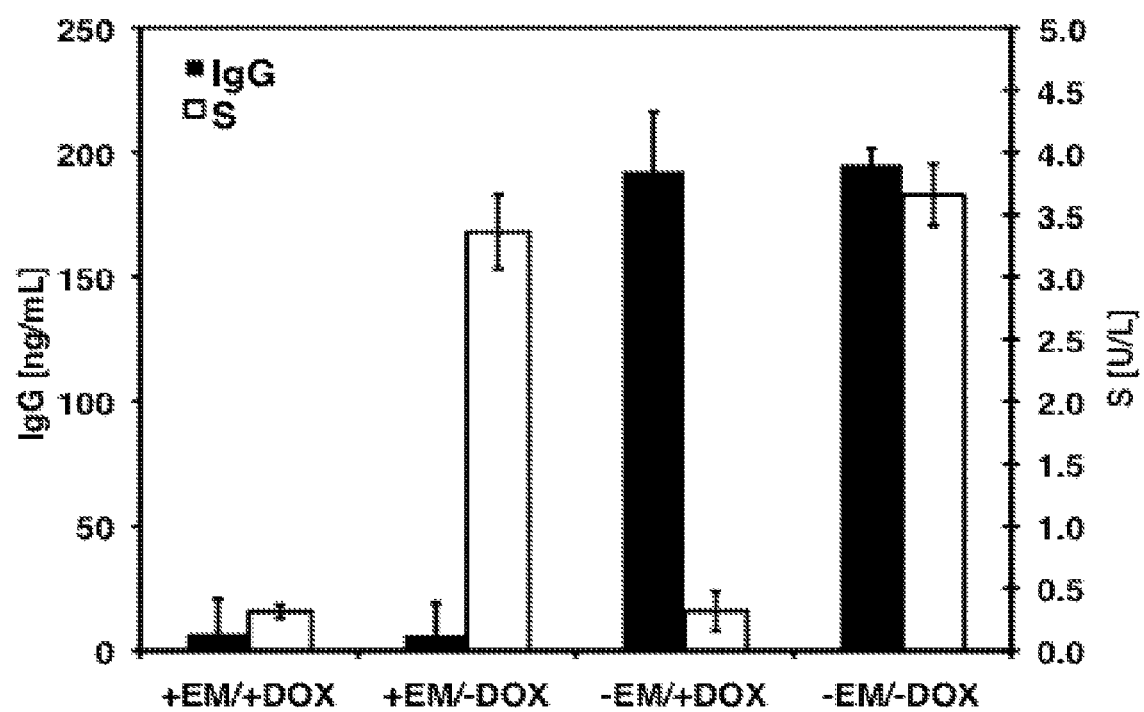

FIG. 5. Co-cultivation of two different capsule populations.

SEAP-producing CHO-SEAP$_{18}$ were co-encapsulated with HEK-301$_9$ and a high molecular weight FITC-Dextran (150 kDa), whereas antibody-producing CHO-B13-24 were co-encapsulated with HEK-260$_{11}$ and a high molecular weight TRITC-Dextran (150 kDa). The two capsule populations were subsequently mixed at a ratio of 1:1 and cultivated under different antibiotic conditions for 5 days. SEAP and IgG levels in the culture supernatant were analyzed for the different conditions 120 hours after seeding the capsules.

Abbreviations: DOX, doxycycline; EM, erythromycin; IgG, immunoglobulin G; S, SEAP production.

FIG. 6. Antibiotic-controlled release of capsule cargo in mice.

(A) SEAP activity in mouse serum 3, 6 and 9 days after intraperitoneal injection of capsules containing concentrated SEAP and HEK-301$_9$ and intraperitoneal administration of doxycycline (+DOX) or PBS (−DOX).

(B) At the same time, capsule populations were cultured in vitro and SEAP expression levels in the supernatant were analyzed every 24 hours. Cell culture medium was exchanged and capsules were washed daily after sample removal.

Abbreviations: DOX, doxycycline; S, SEAP production; t, time.

Figure 7:
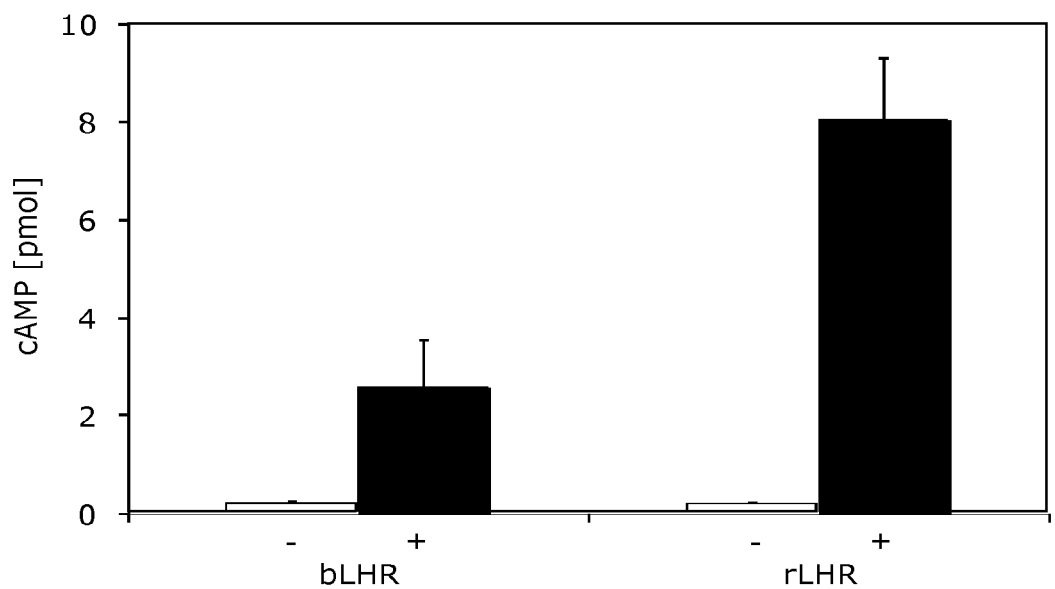

FIG. 7: Increase of intracellular cAMP in response to bLH-activated LHR signaling.

HEK293T cells were transiently transfected for constitutive bLHR or rLHR expression. 48 hours post-transfection the cells were induced by the addition of 500 ng/ml bLH. The intracellular cAMP-levels were determined 1 h post-induction. The presence of bLH resulted in a 12-fold or 29-fold increase in intracellular cAMP when bLHR or rLHR was expressed. (□) no bLH, (■) 500 ng/mL bLH.

Abbreviations: bLH, bovine luteinizing hormone; bLHR, bovine luteinizing hormone receptor; rLHR, rat luteinizing hormone receptor; cAMP, cyclic adenosine monophosphate.

Figure 8:
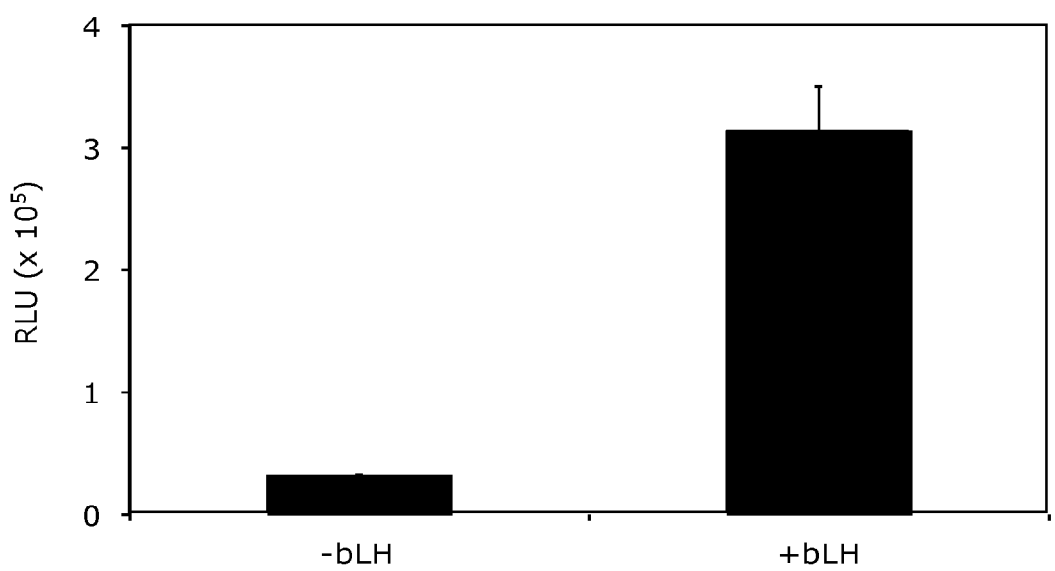

FIG. 8: Bovine LH induced LHR-signaling activates $P_{CRE}$ controlled luciferase expression.

HEK293T cells were transiently transfected for rLHR and $P_{CRE}$ controlled luciferase expression. 24 hours after transfection the cells were transferred to a 96-well plate, cultured for 12 h and induced by the addition of 500 ng/ml bLH. The luciferase expression was measured 6 h post-induction. The induction of the LHR-signaling by bLH resulted in a 9.9±0.1 fold increase in luciferase expression. Luciferase expression was expressed as relative light units (RLU).

Figure 9:
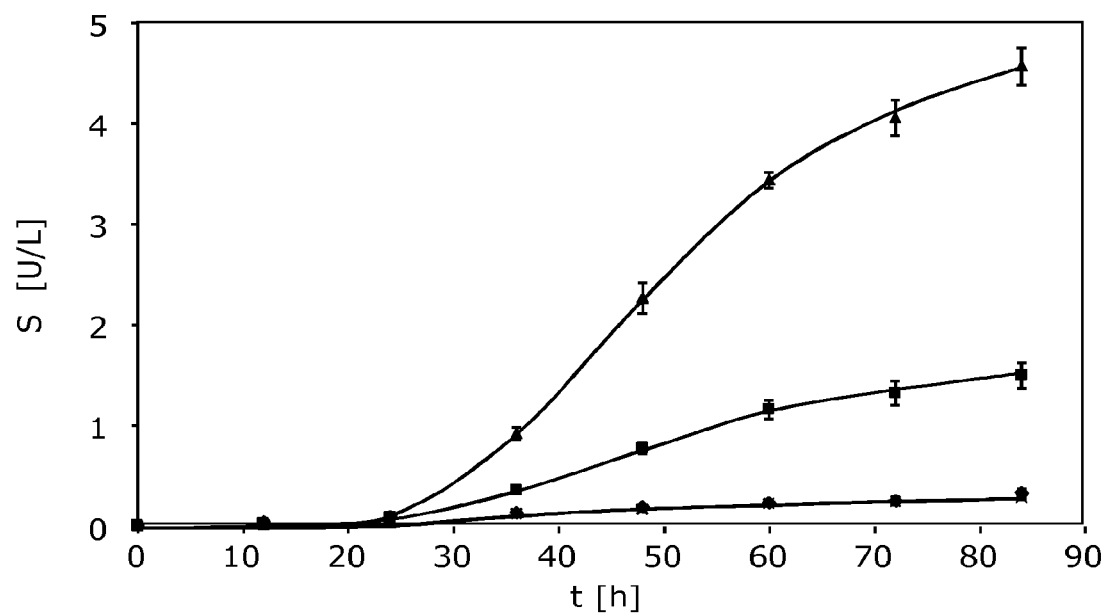

FIG. 9: Time-dependent activation of SEAP expression by LHR-signaling.

HEK293T cells were transiently co-transfected for $P_{CRE}$ dependent SEAP expression and constitutive bLHR- or rLHR expression or with the empty vector pcDNA3.1(+). 24 hours post-transfection the cells were induced by addition of 500 ng/mL bLH or cultivated non-induced. An activation of the LHR-signaling by bLH resulted in an increase in SEAP expression over time. Non-induced cells showed only basal levels of SEAP expression. When the receptor signaling was activated by bLH, cells expressing the rLHR showed a 3-fold higher SEAP production relative to the bLHR-expressing cells. (▲) rLHR+bLH; (■) bLHR+bLH; (×) rLHR-bLH; (♦) bLHR-bLH;

Abbreviations: S, SEAP production; t, time.

Figure 10:
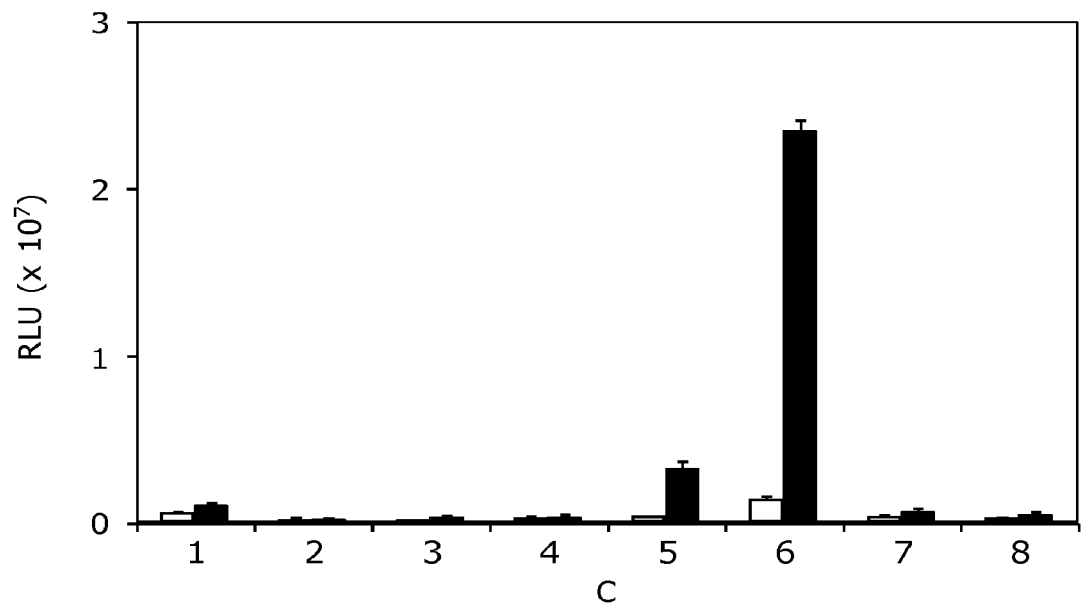

FIG. 10: Clonal selection of stable cell lines engineered for constitutive rLHR expression.

HEK293T cells were cotransfected with pLEN-LHR and pZeoSV2. After clonal expansion several single clones were transiently transfected with pCRE-Luc and screened for the functional expression of rLHR by their ability to respond to bLH. Clone 6 showed best performance and highest bLH-dependent luciferase expression resulting in a 17.0±0.2 induction of luciferase expression in response to bLH. (□) no bLH; (■) 500 ng/ml bLH. Luciferase expression was expressed as relative light units (RLU).

Figure 11:
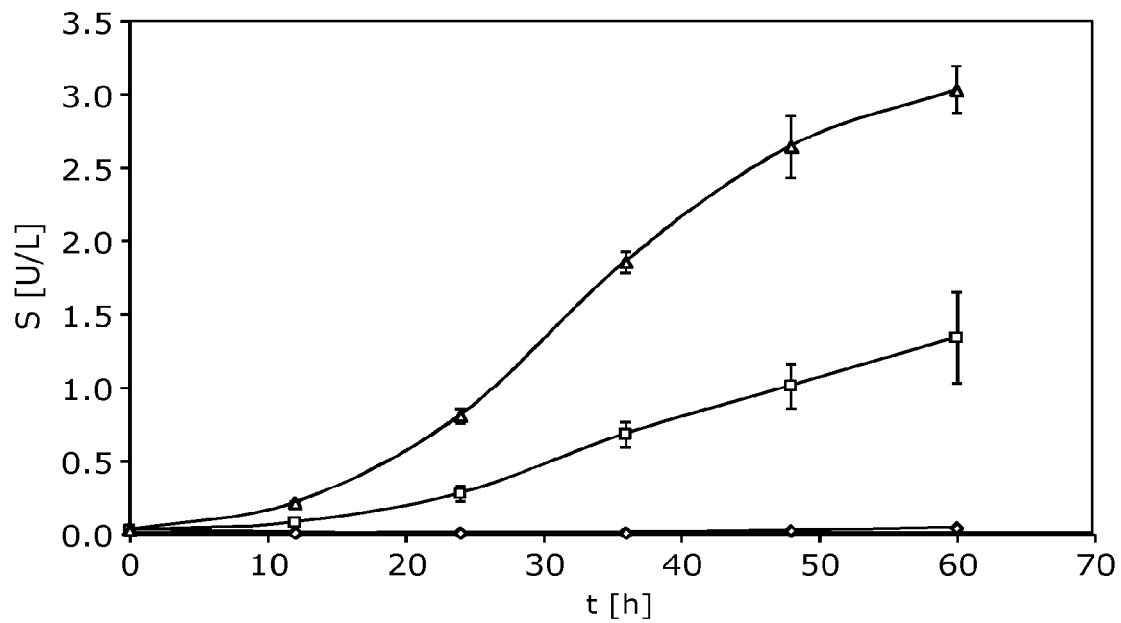

FIG. 11: Bovine LH can penetrate capsules and induces reporter gene expression of encapsulated cells.

Encapsulated CK04 cells transiently transfected for $P_{CRE}$ controlled SEAP expression showed bLH dose-dependent SEAP expression. The SEAP production increased over time in the presence but not the absence of bLH.

(◊) 500 ng/mL bLH; (□) 100 ng/mL bLH; (Δ) no bLH.

Abbreviations: S, SEAP production; t, time

Figure 12:
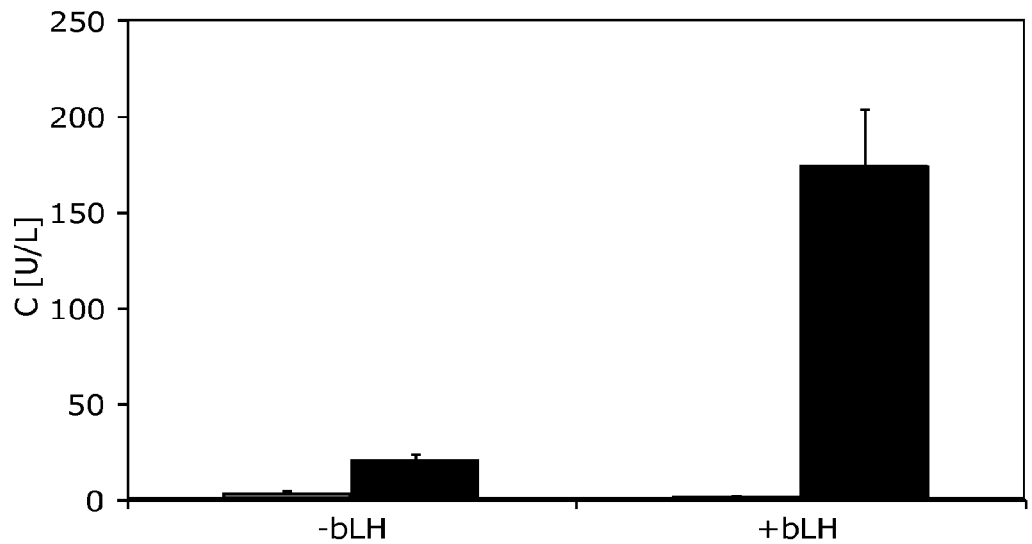

FIG. 12: Bovine LH-induced expression of secreted cellulase.

Cellulase activity assay performed from cell culture supernatants 48 h post-induction. CK04 cells transiently transfected for $P_{CRE}$ controlled cellulase expression (pCK71) or control transfections with an empty vector (pcDNA3.1(+)) revealed an 8.4±0.2 fold bLH-dependent increase in cellulase activity.

(□) CK04 cells transfected with empty pcDNA3.1(+); (■) CK04 transfected with pCK71;

Abbreviations: bLH, bovine luteinizing hormone; C, cellulase activity.

Figure 13:
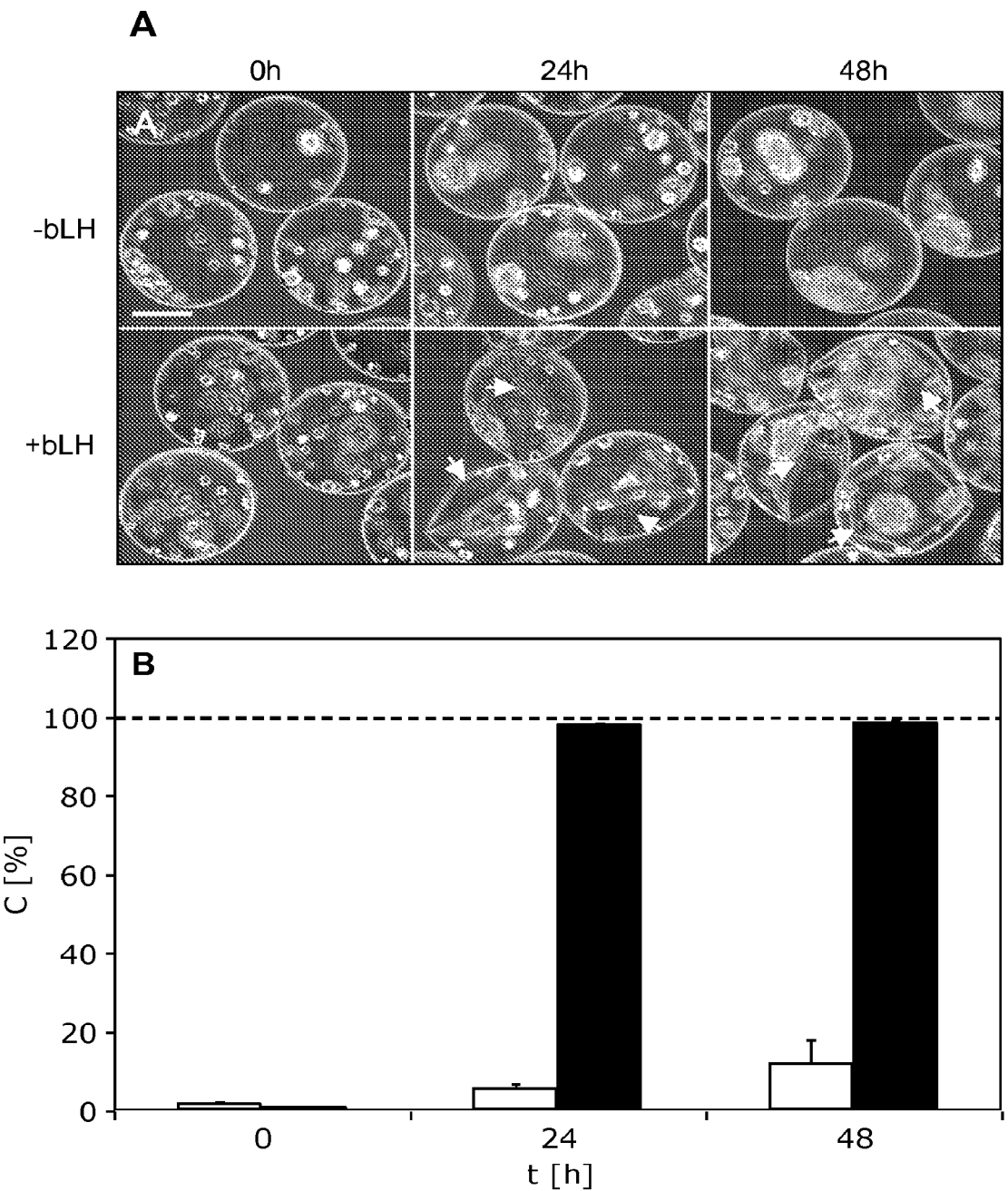

FIG. 13: Bovine LH-dependent disruption of microcapsules.

(A) Phase-contrast photomicrographs of CS/pDADMAC encapsulated CK04 cells transiently transfected for $P_{CRE}$ controlled cellulase expression (pCK71, $P_{CRE}$-cellulase-pA). The microcapsules were cultured in the absence or presence of 500 ng/ml bLH. In the presence of bLH the capsules were disrupted by the induced expression of cellulase whereas the non-induced capsules remained intact. Arrows indicate the disrupted capsules.

(B) Quantification of microcapsule disruption. Per sample approximately 150 capsules were counted and the amount of capsule disruption was calculated. 24 hours post-induction 98% of the capsules were disrupted by the induced cellulase. However, in the absence of bLH only 6% of capsules showed spontaneous degradation.

Abbreviations: bLH, bovine luteinizing hormone; C, cellulase activity; t, time.

Figure 14:
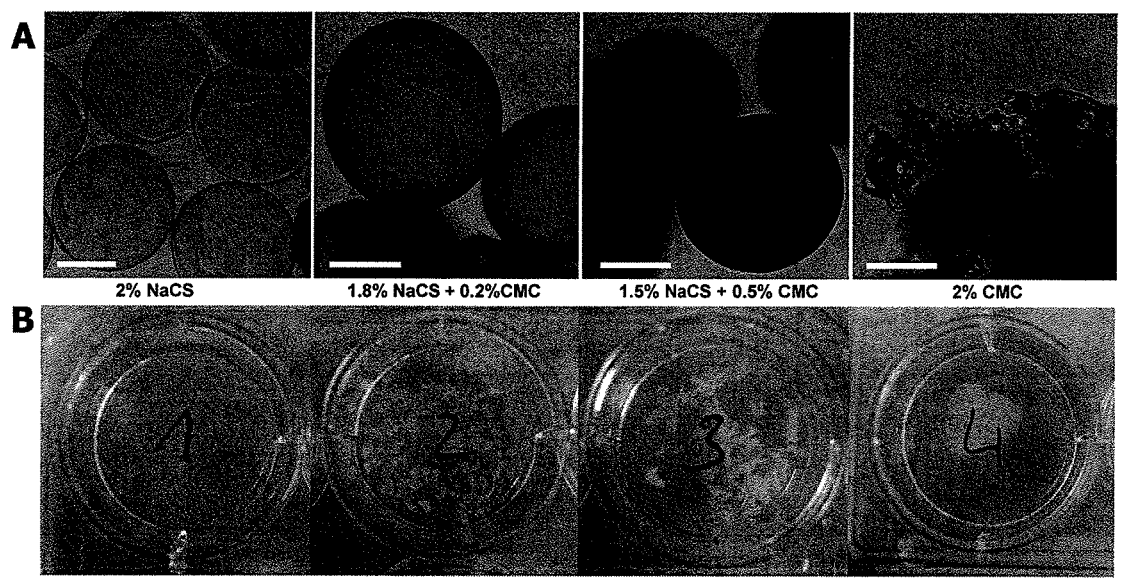

FIG. 14: NaCS microcapsule formation with increasing CMC concentrations.

(A) Microcapsules were produced using the automated Inotech encapsulation protocol. An increase in CMC resulted in less transparent capsules with a higher stability. However, in the absence of NaCS (2% CMC) no capsules were formed. The scale bar represent 100 μm.

(B) Clustering of the microcapsules shown in FIG. 14A. Microcapsules composed of 2% NaCS were non-sticky and did not cluster (1). Increasing concentrations of CMC resulted in enhanced stickiness of capsules and cluster formation (2,3). In the absence of NaCS no capsules were formed (4).

DETAILED DESCRIPTION OF THE INVENTION

The invention relates to a semipermeable microcapsule consisting of a polymer degradable by a polypeptide comprising a genetically engineered cell expressing said polypeptide in response to a triggering compound, and optionally one or more compounds of interest.

A "microcapsule" according to the invention means a sphere with a diameter between 10 and 2000 μm consisting of a hydrogel formed by polymers. The pore size of the hydrogel has a molecular weight cut-off between 5 and 500 kDa. The microcapsule can either be solid or contain a liquid core.

The polymer is selected from the group consisting of oligosaccharides, oligopeptides, oligonucleotides, polyesters and polyamides, and mixtures thereof with each other and with other organic polymers.

Suitable oligosaccharides are, for example, cellulose, starch, lignin, chitin, chitosan, or dextran. Suitable oligopeptides are, for example, fibrin, collagen or poly-L-lysine. Suitable oligonucleotides are, for example, DNA or RNA. Suitable polyesters are, for example, polyhydroxybutyrate or poly-lactic acid. Suitable polyamides are, for example, polyacrylamide or poly(phenylene phtalamide).

Examples of polymers and corresponding polypeptides degrading these polymers are: Alginate—alginase, starch—amylase, chitosan—chitosanase, dextran—dextranase, collagen—collagenase, protein-based polymers (oligopeptides)—protease, DNA-based polymers—DNAse, polyester-based polymers—esterase, polyamide-based polymers—amidase.

Any of the mentioned polymers may contain a chemical modification, for example, sulphate groups or phosphate groups favouring precipitation and formation of the capsules.

The definition of polymers includes hybrid polymers consisting of polymers as defined above and further a second polymer which is non-degradable. Examples are polyethylene glycol- or polyacrylamide-based polymers incorporating sequences degradable by a polypeptide as listed above.

In a particular preferred embodiment the polymer is cellulose or a cellulose derivate and the polypeptide is cellulase.

"Degradable by a polypeptide" according to the invention means that the microcapsule breaks apart and releases compounds and cells from the interior on treatment with the polypeptide within a reasonable period of time, for example within 48 hours at ambient temperature suitable for the cells.

The preferred polymer degradable by cellulase is a mixed polymer comprising cellulose or a cellulose derivative, for example cellulose sulphate or cellulose phosphate, or mixtures of cellulose sulphate and 0.01 to 5% carboxymethyl cellulose of a molecular weight between 50'000 and 500'000, and a second polymer precipitating the first one suitable for microcapsule formation, for example poly-diallyldimethyl ammonium chloride or poly-L-lysine. The properties of the preferred polymer are such that the microcapsules formed are semipermeable and biocompatible. A particularly preferred polymer is sodium or potassium cellulose sulfate (CS)/poly-diallyl-dimethyl-ammonium chloride (pDADMAC). Microcapsules from this polymer are usually prepared from a solution containing 1-3%, e.g. around 2%, cellulose sulphate and 0.5-7%, preferably 1-5%, diallyl-dimethyl-ammonium chloride. Another particularly preferred polymer is sodium cellulose sulfate (CS) modified with carboxymethyl cellulose (CMC)/poly-diallyl-dimethyl-ammonium chloride (pDADMAC). Microcapsules from this polymer are usually prepared from a solution containing 1-3%, e.g. around 1.8%, cellulose sulphate, 0.01-1.5%, e.g. around 0.2%, carboxymethyl cellulose, and 0.5-7%, preferably 1-5%, diallyl-dimethyl-ammonium chloride. The addition of carboxymethyl cellulose (CMC) results in more stable and opaque microcapsules. The higher the CMC concentration the higher the stickiness of the capsules, which then create microcapsule clusters.

The particular example of the preferred microcapsule breaks apart and releases compounds and cells from the interior on treatment with bacterial or fungal cellulase, for example *A. niger* cellulase, at a concentration of 1 U/ml within 1 hour at 37° C.

"Semipermeable" according to this invention means that low molecular weight compounds, for example with a molecular weight below 10-50 kDa, in particular below 20-40 kDA, such as below approx. 30 kDa, may easily cross the membrane of the semipermeable microcapsules, whereas high molecular weight compounds may not do so. As a result of this, nutrients required by encapsulated cells to survive and further develop may cross the capsule membrane, whereas larger molecules, for example antibodies, cell degrading enzymes or components of the immune system, such as T-cells or the complement system, may not cross. The molecular weight cut-off may be regulated by changing the amount of crosslinking during precipitation, or using a different polymer resulting in different pore sizes. Examples of other suitable polymers is cellulose with another degree of substitution with sulphate.

"Biocompatible" according to the invention means that the microcapsules are non-toxic, do not elicit an immunological response and have an average half life time of at least 1 day in animals, in particular mammals, including man.

"Triggering compound" is a chemical or biological compound influencing the expression of the desired polypeptide or compound of interest in a genetically engineered cell expressing said polypeptide or the compound of interest, respectively. Influencing means either activating or suppressing expression. A triggering compound may be a compound introduced, such as a drug, in particular an antibiotic, or an endogenous compound of the animal for which the microcapsules are designed, in particular a mammal including man, such as a hormone or a natural endogenous signalling compound appearing during a disease or abnormal condition. Excluded from the meaning of "triggering compounds" are compounds that are omnipresent in physiological systems, for example, water, inorganic salts, such as sodium, potassium, calcium, magnesium and ammonium chloride, carbonate, nitrate, sulphate, and phosphate, and the corresponding acids and bases, acetates and acetic acid, malonates and malonic acid, and simple sugars, such as hexoses and pentoses.

Examples of expression systems and corresponding triggering compounds are, for example, the E.REX system triggered by macrolide antibiotics, the TET systems triggered by tetracycline antibiotics, the UREX system triggered by uric acid, the PEACE system triggered by phloretin, the PIP System triggered by streptogramin antibiotics, the AIR system triggered by acetaldehyde, the Q-mate system triggered by cumate, the NICE system triggered by 6-hydroxynicotine, the lac system triggered by IPTG, the REDOX system triggered by NADH, the QuoRex system triggered by SCB1, the RhIR, TraR and LasR systems triggered by homoserinelactones, the steroid-hormone responsive systems triggered by steroid hormones and analogs thereof, the GyrB-systems triggered by aminocoumarin antibiotics, the FKBP-based systems triggered by rapamycin, FK506 and analogs thereof (rapalogs), the recombinase (Cre, Flp)-based system triggered by steroid hormones and analogs thereof, the $F_M$-based secretion system triggered by rapamycin and analogs thereof, the aptamer-based system triggered by dye-like molecules, the ribozyme system triggered by toyocamycin, the elF4G-based systems triggered by farnesyltransferase inhibitors or rapamycin and analogs, the enzyme dimerization system triggered by dimerizer drugs (all described in Weber W, Fussenegger M, Handb Exp Pharmacology 2007; 178:73-105), the heavy metal based system triggered by heavy metal ions (Fussenegger M, Biotechnology Progress 2001; 17(1):1-51), the ART system triggered by arginine (Hartenbach S, Daoud-El Baba M, Weber W, Fussenegger M, Nucleic Acids Res 2007; 35(20):e136) and the biotin systems triggered by biotin (Weber W, Bacchus W, Daoud El-Baba M, Fussenegger M, Nucleic Acids Res 2007; 35(17):e116).

Preferred expression systems and corresponding triggering compounds are the E.REX system triggered by macrolide antibiotics, the TET systems triggered by tetracycline antibiotics, the PIP system triggered by streptogramin antibiotics, and the FKBP and the $F_M$ system triggered by rapalogs.

The particular example of luteinizing hormone receptor/luteinizing hormone as a signalling compound in mammals is described in Ascoli M, Fanelli F, Segaloff D L, Endocrine Reviews 2002; 23(2):141-74.

"Compounds of interest" is, for example, a therapeutic compound (drug), for example of a molecular weight above 1 kDa or 10 kDa, such as peptidic therapeutics, antibodies, darpins, natural or modified hormones, natural or modified enzymes. Further compounds of interest are biopolymers, e.g. oligonucleotides, oligopeptides, oligosaccharides, or biologics, e.g. sperm, drug loaded liposomes, vaccines, viruses, viral vectors, or any eukaryotic or prokaryotic cell. The compounds of interest may be encapsulated in the microcapsules of the inventions as such, or may be expressed and secreted by an encapsulated genetically engineered cell responding to a triggering compound as defined above. Expression and secretion by a genetically engineered cell is preferred if the compound of interest comprises a polypeptide. Examples of useful polypeptide-comprising compounds of interest expressed are antibodies or derivatives thereof, enzymes, hormones, cytokines, receptors and derivatives thereof. Microcapsules may contain one or more, e.g. two, three or four, compounds of interest, or a compound of interest and a cell line expressing a further compound of interest, or two or three cell lines expressing two or three different, compatible compounds of interest. Compounds of interest may also be marker compounds, either as marker to demonstrate the functionality of a particular system according to the invention, or as markers co-expressed from a particular cell line together with a further compound of interest. Examples of marker compounds are markers detectable by spectroscopic methods, for example fluorescent markers, such as green fluorescent protein (GFP) or yellow fluorescent protein (YFP), or also marker proteins detectable and quantifiable by an enzyme reaction such as luciferase, human placental secreted alkaline phosphatase (SEAP) or specific antibodies.

Preferred compounds of interest are biologics, whole cells and viral vectors.

The polypeptide degrading the polymer is any polypeptide compatible with the cells expressing said polypeptide and able to degrade the polymer. Such polypeptides include, for example, alginase, for the degradation of alginate, amylase, for the degradation of starch, chitosanase for the degradation of chitosan, dextranase for the degradation of dextran, collagenase for the degradation of collagen, protease for the degradation of polypeptides, DNAse for the degradation of oligonucleotides, esterase for the degradation of polyesters, and amidase for the degradation of polyamides.

A preferred polypeptide for degradation is cellulase. "Cellulase" expressed by a genetically engineered cell in response to a triggering compound is any type of cellulase compatible with mammalian cells, including modified cellulases and cellulase derivatives retaining the cellulase property. A preferred cellulase is cellulase from *Bacillus subtilis*, such as *B. subtilis* (1-4)-beta-glucanase, and derivatives thereof retaining the cellulase property. Preferred derivatives are chimeric compounds of the cellulase with a mammalian secretion signal protein. Other cellulases comprise, for example, exo-1,4-beta-D-glucanases, endo-1,4-beta-D-glucanases, and 1,4-beta-D-glucosidases. In the case of hemicellulose other enzymes are able to degrade the polymer structure, for example arabinases, or xylanases. A particularly preferred cellulase is cellulase called SecCell, a chimeric protein consisting of *B. subtilis* (1-4)-beta-glucanase and the signal sequence derived from the murine Igk-chain V-12-C region.

The two-component controlled release technology according to the invention consists of a biocompatible polymer microcapsule and a transgenic sensor cell line engineered for trigger-inducible expression of a chimeric secreted cellulase which catalyses capsule breakdown thereby enabling the release of one or more compounds of interest, in particular biopharmaceuticals produced by co-encapsulated producer cells. This approach is exemplified by the trigger-induced release of compounds of interest from biocompatible CS-pDADMAC or CS-CMC-pDADMAC capsules. Capsule rupture and the accompanying cargo release is controlled by the inducible expression of a modified bacterial cellulase (SecCell) from mammalian sensor cells. The functionality of the system is proven by engineering sensor cells that express SecCell under the control of either doxycycline or erythromycin responsive promoters. After induction, with the corresponding antibiotic, SecCell is expressed and secreted from the sensor cells and causes the destabilization of the capsule, rupturing the capsule and releasing its contents. Model glycoproteins, either expressed by co-encapsulated cells or co-encapsulated purified factors, are able to be released from capsules upon induction in vitro as well as in vivo. This technology according to the invention opens new possibilities for trigger-induced release of therapeutic cargos. By combining the system of the invention with available gene-regulation systems the tools are created to utilize a broad variety of cues to control the release of compounds of interest such as biologics in therapeutic settings.

Disruption of the microcapsules may be from the inside, or from another kind of microcapsule by excretion of the disrupting polypeptide, which then breaks down the microcapsule carrying the compound of interest.

In a particular application of the invention a hormone-responsive microcapsule degradation system is created to overcome the challenges of artificial insemination (AI). Hormone-inducible CS/pDADMAC or CS-CMC/pDADMAC capsule disruption is demonstrated by sensing the specific preovulatory bovine luteinizing hormone (bLH) surge. Combining the novel bLH-dependent capsule degradation technology with the encapsulation of bull sperm will increase efficiency of AI. The encapsulation protects inseminated sperm from an unfavourable environment in utero while a bLH-inducible capsule degradation releases the sperm immediately at the time of ovulation. In a further embodiment the hormone-responsive microcapsule may further comprises cells expressing a fucosyltransferase and annexins, preferably annexin 1 or 5, which promote sperm binding and prolong sperm survival.

The invention therefore further relates to a method of artificial insemination comprising administering to a female animal (including human) an effective amount of a microcapsule consisting of a polymer degradable by cellulase comprising sperm and a cell expressing cellulase triggered by luteinizing hormone. In a further embodiment the invention relates to a method of artificial insemination comprising administering to a female animal (including human) an effective amount of a microcapsule consisting of a polymer degradable by cellulase comprising sperm, a cell expressing cellulase triggered by luteinizing hormone and a cell expressing fucosyltransferase and/or annexins, preferably annexin 1 or 5.

Capitalizing on the preferred established optionally modified cellulose sulfate (CS)/poly-diallyldimethyl ammonium chloride (pDADMAC)-based precipitation chemistry, a high-throughput protocol for the production of microcapsules containing compounds of interest and/or cells producing such compounds is established. The preferred CS-pDADMAC polymers and CS-CMC-pDADMAC polymers are known for their high biocompatibility, lack of cytotoxicity and their cheap and straightforward production protocols. Owing to their covalent polymer structure and their chemistry, implanted CS-pDADMAC or CS-CMC-pDADMAC capsules are inert to metabolic breakdown and survive for several months in vivo.

Cellulases, which can cleave the polymer backbone of CS-pDADMAC or CS-CMC-pDADMAC capsules, are typically absent from mammalian tissues. In a preferred embodiment a *Bacillus subtilis* (1-4)-beta-glucanase (cellulase) is engineered by the N-terminal fusion to an IgG-type secretion signal sequence with expression placed under control of the TET [Gossen M, Bujard H, Proceedings of the National Academy of Sciences USA 1992; 89(12):5547-51] or E.REX [Weber W, Fux C, Daoud-el Baba M, Keller B, Weber C C, Kramer B P, Heinzen C, Aubel D, Bailey J E, Fussenegger M, Nature biotechnology 2002; 20(9):901-7] systems for trigger-inducible expression and secretion by mammalian cells. TET and E.REX are prototypic transgene control system which are responsive to clinically licensed antibiotics (tetracycline/doxycycline, erythromycin) and consist of chimeric transactivators (tTA and ET1, respectively), designed by fusing bacterial response regulators (TetR and E, respectively) to a eukaryotic transactivation domain (VP16), which binds and activates promoters ($P_{hCMV^*-1}$ and $P_{ETR}$, respectively) containing transactivator-specific operator sites (tetO$_7$ and O$_{ETR}$, respectively) 5' of minimal eukaryotic promoters. In the presence of regulating antibiotics the transactivators are released from their cognate promoters and transgene expression is silenced in a dose-dependent manner. TET and E.REX systems have been shown to be compatible and can be used for independent control of different transgenes in a single mammalian cell or mixed cell populations.

Therapeutic interventions using novel drug carriers are being continuously designed to overcome limitations in traditional drug delivery. To avoid multiple dosing and to sustain a therapeutic level of the active drug over a prolonged period of time, different approaches have been established: (i) drug-containing implants, (ii) micro-pumps, (iii) encapsulation of cell lines or primary cells continuously producing biologics, (iv) biodegradable polymers containing embedded therapeutic substances or (v) implants of drug-containing capsules designed to rupture in response to biological, chemical or physical stimuli. The present invention complements and further improves such novel approaches.

Co-encapsulating sensor cells, engineered for TET or E.REX-controlled expression of the secreted mammalian cellulase, with cell lines producing compounds of interest into CS-pDADMAC capsules, trigger-controlling capsule rupture and fine-tuning release kinetics of protein therapeutics in vitro as well as in mice is demonstrated in the particular examples described below. Active bacterial cellulases can be efficiently expressed in mammalian cells without showing significant cytotoxicity. Enzyme-induced breakdown of physiologically inert polymer capsules triggering the release of the encapsulated material represents a powerful tool to precisely adjust time and delivery kinetics of compounds of interest to therapeutic requirements. The technology of the invention is therefore useful for timely delivery of specific therapeutic doses in gene therapy tissue engineering and other therapeutic applications.

By varying the relative cellulose-sulfate/pDADMAC or cellulose sulfate-CMC-pDADMAC concentrations and production parameters capsule porosity can be tuned for selective retention of specific biological compounds of interest while sustaining cell growth and viability by a free flow of nutrients and waste product across the capsule membrane. The preferred molecular weight cut-off between 25 and 40 kDa enables retention of most protein therapeutics including IgGs. The microcapsules of the invention may either accommodate biological compounds of interest or cells producing desired protein therapeutics. Microencapsulation of therapeutic proteins requires separate production and downstream processing efforts making drug delivery as expensive as classic injection-based therapies. In situ production of biological compounds by microencapsulated cells alleviates classical biopharmaceutical manufacturing and makes therapy more efficient and affordable, although sensor and producer cells released into the body have to be carefully selected in order not to cause problems in a patient. The studies using xenotypic cell lines in mice did not reveal any immediate adverse effects in the animal. Alternatively, the use of autologous cells may completely eliminate concerns about side effects of heterologous cell material.

The recently developed protein-transducing nanoparticles also enable simultaneous production and encapsulation by packaging of therapeutic proteins into lentivirus-derived nucleic acid-free nanoparticles [Link N, Aubel C, Kelm J M, Marty R R, Greber D, Djonov V, et al., Nucleic acids research 2006; 34(2):e16]. However, in comparison to the technology of the present invention, protein-transducing nanoparticles release their therapeutic cargo in an uncontrolled manner directly upon contact into any cells, which, unlike in the present invention, lacks release control and limits therapeutic impact to intracellular targets.

The present technology is straightforward, robust and advantageous for the following reasons: (i) The preferred CS-pDADMAC and CS-CMC-pDADMAC capsules and related capsules can be produced at low cost and large scale using multi-nozzle devices for production of clinical-grade capsules. (ii) Capsule parameters such as molecular weight cut-off and cellulose content can easily be varied to modify growth and production characteristics inside capsules and adjust release kinetics. (iii) The availability of an engineered ready-to-use sensor cell line transgenic for trigger-controlled SecCell production increases flexibility as this cell line can be co-encapsulated with any established constitutive or regulated producer cell line or primary cell via co-encapsulation. The relative number of encapsulated sensor and producer cells can be used to adjust drug-release kinetics. For one-cell line solutions producer cells can also be engineered for regulated SecCell expression. (iv) The preferred TET and E.REX systems used to trigger SecCell expression, capsule rupture and release of compounds of interest make the system of the invention compatible with any transcription control system. (v) Release kinetics can be modified by timing and dosing of the SecCell trigger molecules. (vi) The unique characteristic of SecCell or related cellulases to exclusively breakdown microcapulses of the invention such as CS-pDADMAC or CS-CMC-pDADMAC capsules internally and leave the outer surface of the capsule intact makes the technology of the invention suitable for the administration of mixed capsule populations, which differ, for instance, in the type and number of sensor cells, thereby allowing the controlled release of different compounds of interest at different points in time and with different release kinetics without having to repeat capsule administration. (vii) Although in the specific TET and E.REX examples antibiotics are used as a heterologous inducer in vivo, it has likewise been demonstrated that the system of the invention can be triggered by endogenous signals such as luteinizing hormone (LH). Likewise it will be possible to connect the system of the invention to other endogenous signals, which are increased during a disease or infection state, e.g., hormone or interleukins, to trigger release of therapeutic compounds of interest and provide a rapid and self-sufficient first-line protection.

The invention further relates to a method of treating a disease comprising administering to a patient in need thereof a therapeutically effective amount of a microcapsule consisting of a polymer degradable by a polypeptide comprising a therapeutic drug against the disease and a cell expressing said polypeptide triggered by a signalling compound for the disease.

A particular example of a construct useful for erythromycin and doxycycline regulation is as follows:

Design and Characterization of a Secreted Mammalian Cellulase

Figure 1A:
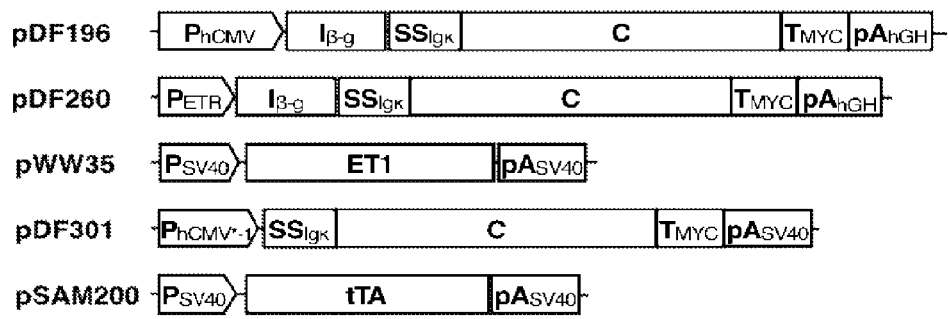
FIG. 1. Transient expression of modified *B. subtilis* cellulase in mammalian cells.
Figure 1B:
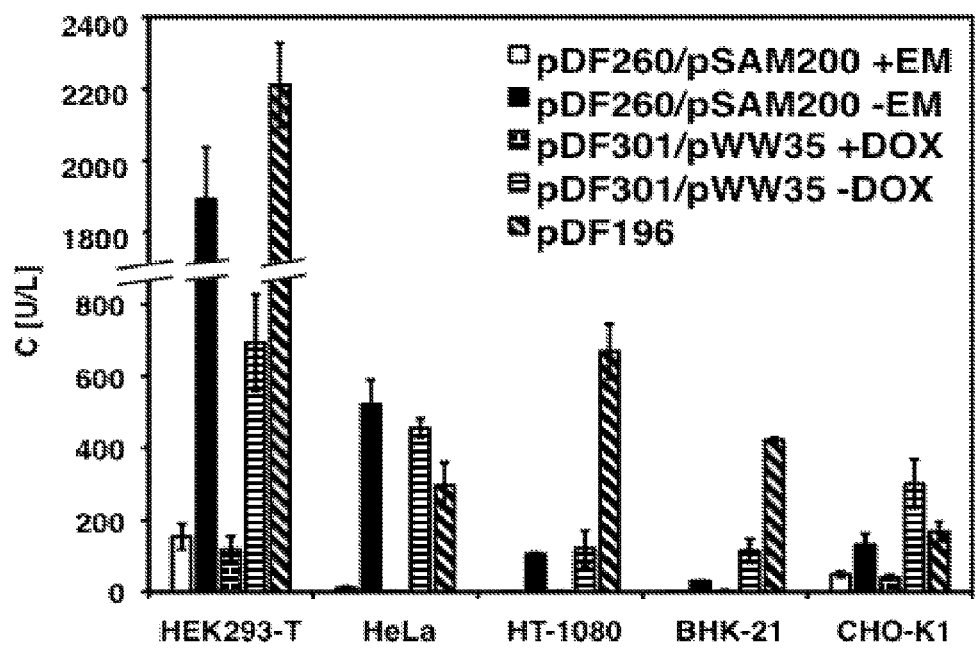

The *Bacillus subtilis* endo (1-4)-beta-glucanase was PCR-amplified from genomic DNA and fused to a strong mammalian secretion signal sequence derived from the murine Igk-chain V-12-C region. The secreted cellulase (SecCell) was cloned downstream of a constitutive promoter ($P_{hCMV}$) as well as two different inducible promoters which enabled doxycycline-($P_{hCMV^*-1}$) and erythromycin-($P_{ETR}$) adjustable transgene expression (FIG. 1A). Transient transfection of SecCell into different human (HEK293-T, HeLa, HT-1080) and hamster (CHO-K1 and BHK-21) cell lines resulted in high-level cellulase activity in the culture supernatants unless SecCell production was repressed by doxycycline (DOX) or erythromycin (EM) (FIG. 1B).

Figure 1C:
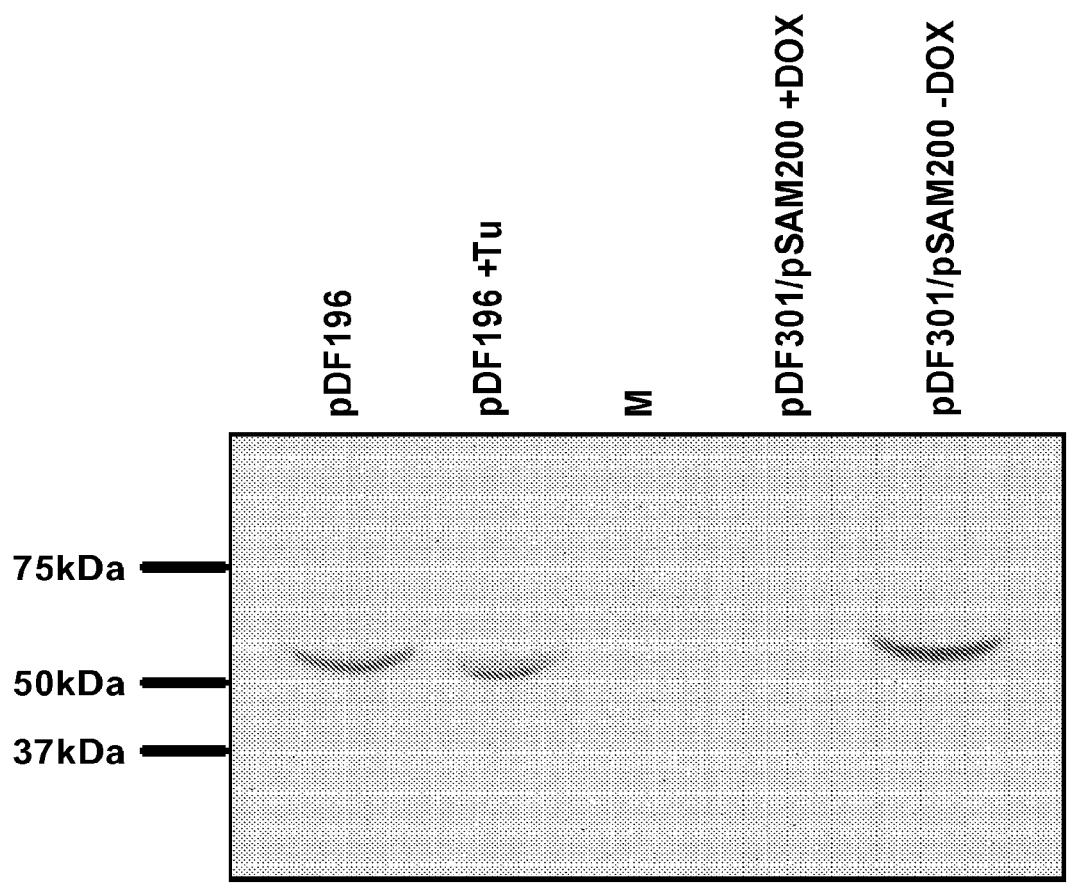

The apparent size of the modified cellulase as well as possible glycosylation was assayed by producing SecCell in HEK293-T in the presence and absence of the glycosylation inhibitor tunicamycin. Western blot analysis of culture supernatants showed that the SecCell produced from tunicamycin-free cultures had a molecular weight of 55 kDa which was lower when the cells were treated with tunicamycin. This suggested that the cellulase was glycosylated in mammalian cells (FIG. 1C).

Figure 1D:
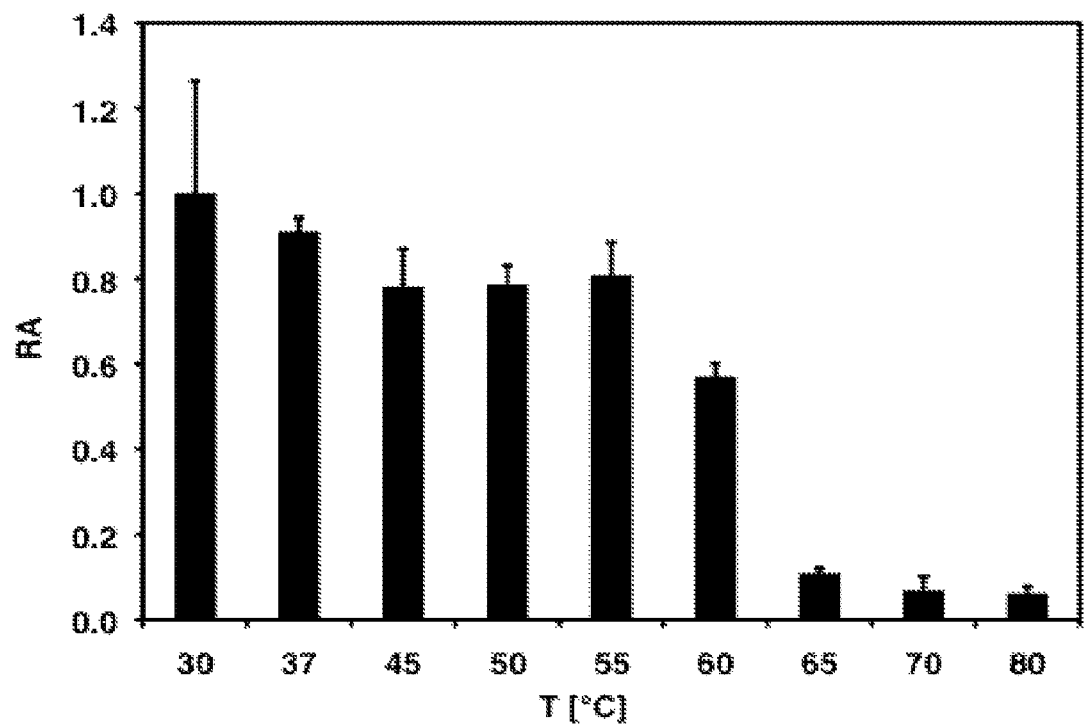
Figure 1E:
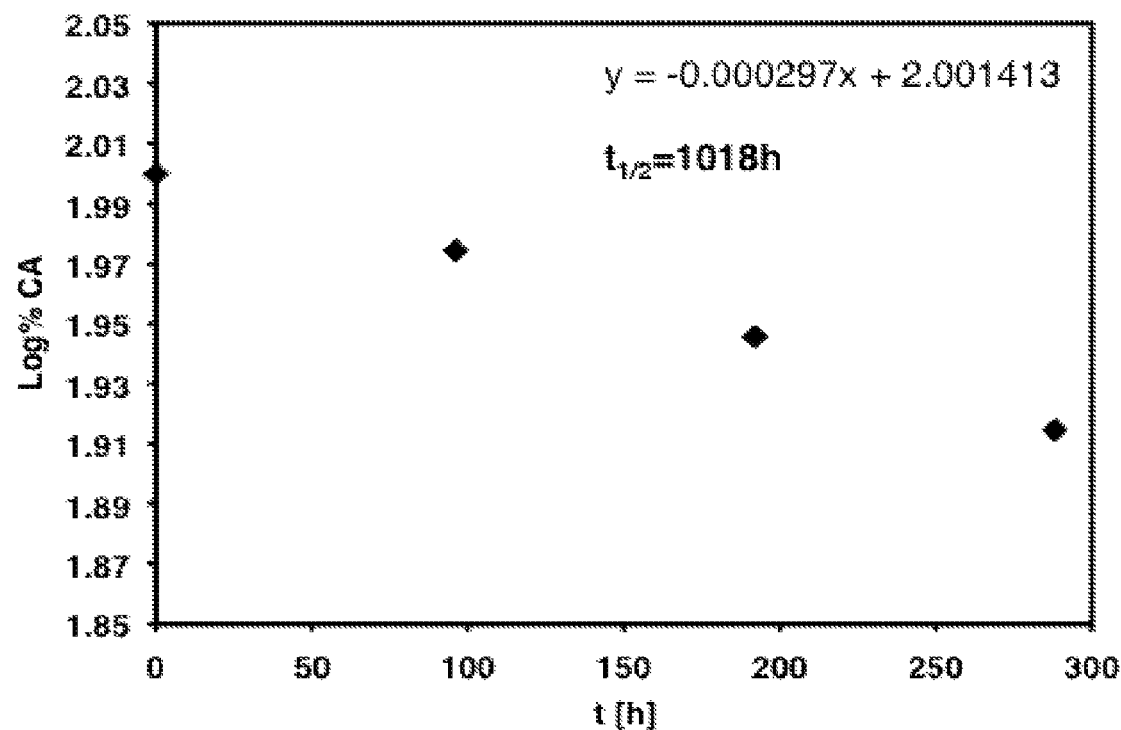

Cellulase properties were further explored by assaying enzymatic activity after incubation at different temperatures. Activity was relatively constant between 30 and 55° C. but dropped sharply upon incubation above 60° C. (FIG. 1D). The stability of the modified cellulase in human serum was also assayed by mixing HEK293-T-produced enzyme with human AB serum before incubating the mixture for a total period of 12 days during which samples were taken every 96 hours (FIG. 1E). The enzymatic half-life was calculated by linear regression of decreasing enzymatic activities to be around 42 days, which is comparable to other secreted proteins of bacterial origin.

Capsule Properties and Rupture Characteristics

Cellulose sulfate capsules were incubated for 16 hours in the presence of FITC-dextran solutions of different molecular weight. After incubation, capsules were washed thoroughly and then analyzed by fluorescence microscopy. Fluorescence micrographs show strong signals for the two FITC-dextrans of lower molecular weight (10 kDA and 20 kDA) and no signal for FITC-dextrans of higher molecular weight (40 kDa, 70 kDa), indicating a molecular weight cut-off between 20 and 40 kDa for the 2% capsules. Upon incubation of 2% CS-containing capsules for 30 minutes at 37° C. with cellulases of the same target specificity, either *Aspergillus niger* cellulase (MW 25 kDa, below molecular weight cut-off) or SecCell (50 kDa, above molecular weight cut-off) only the *A. niger* cellulase was able to trigger capsule rupture at concentrations as low as 1 U/ml. The larger-sized SecCell which is above the molecular weight cut-off and unable to penetrate the capsules failed to induce capsule degradation even at 5 U/ml (FIG. 2). This observation indicates that capsule breakdown can only be initiated from the inside and not from the outside. According to the invention the cellulase (in particular SecCell) is co-encapsulated or produced inside the capsules in order to control capsule breakdown and release of microencapsulated drugs in a robust and reliable manner. Furthermore, this enables sequential or independent release of various compounds of interest using different trigger compounds.

Trigger-Inducible Capsule Rupture and Protein Release

Figure 3:
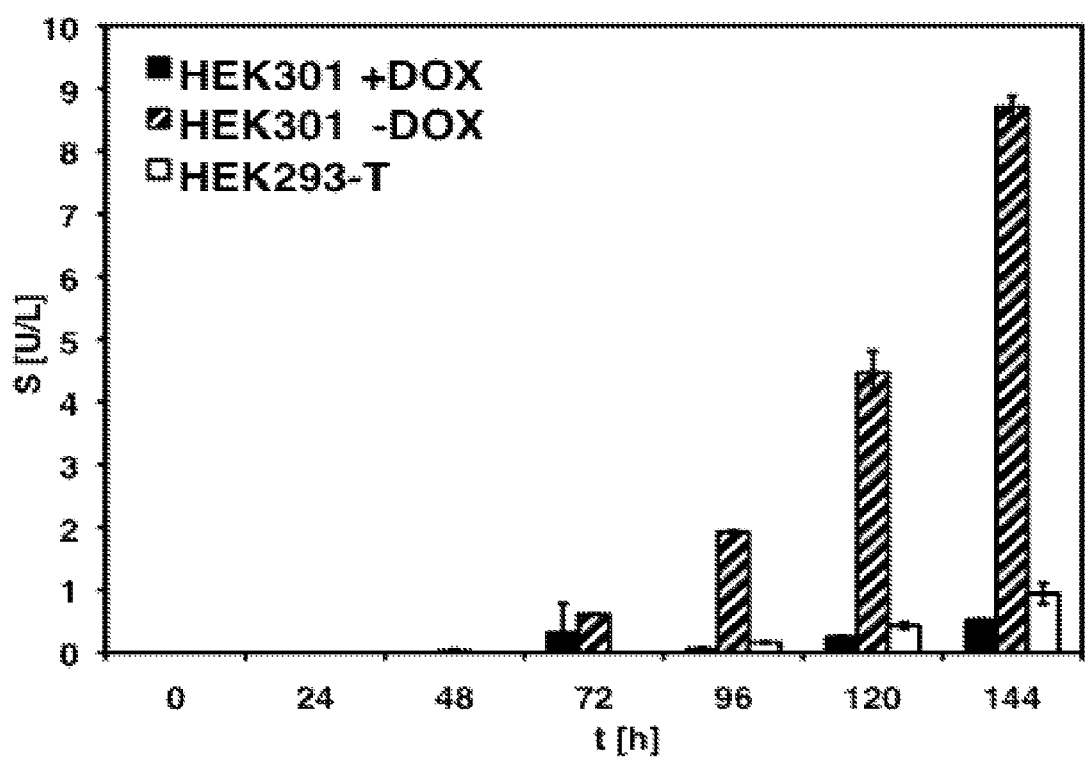

In order to establish and characterize trigger-inducible release of protein drugs, HEK-301$_9$ ($5 \times 10^5$ cells/ml of CS), transgenic for tetracycline-responsive SecCell expression, and CHO-SEAP$_{18}$ ($2.5 \times 10^5$ cells/ml of CS), engineered for constitutive SEAP (58 kDa, above molecular weight cut-off) production were co-encapsulated into CS-pDADMAC capsules and cultivated for 6 days in the presence or absence of doxycycline (DOX). Control capsules contained the same number of the parental cell line HEK293-T instead of the SecCell producing HEK-301$_9$ and CHO-SEAP$_{18}$. Every 24 hours, capsule micrographs were taken and accumulated SEAP activity was assayed in the supernatant. Capsules cultivated in the absence of DOX (maximum induction of SecCell in HEK-301$_9$) started to collapse after an initial lag phase of around 36 hours after encapsulation, leading to a strong increase in SEAP activity in the supernatant compared to intact capsules cultivated in the presence of DOX (repression of SecCell in HEK-301$_9$) (FIG. 3). The control capsules containing CHO-SEAP$_{18}$ cells together with parental HEK293-T behaved in exactly the same manner as the CellEase capsules containing HEK-301$_9$ in which SecCell was repressed by doxycycline (FIG. 3).

The induction of cellulase expression leads to destabilization and rupture of the capsules followed by discharge of their contents. To illustrate the capsule breakdown, two time-lapse microscopy experiments were performed; they revealed (i) the immediate rupture of a cellulose sulfate capsule after addition of cellulase solution (*A. niger* cellulose, MW 25 kDa) and (ii) that the rupture process was triggered after 36 hours by encapsulated HEK-301$_9$. Capsules with SecCell production fully induced were traced by co-encapsulating 150 kDa FITC-dextran whereas negative-control capsules containing HEK293-T were not fluorescently labelled.

Adjusting Protein Release by Fine-Tuning Capsule Rupture Kinetics

Figure 4A:
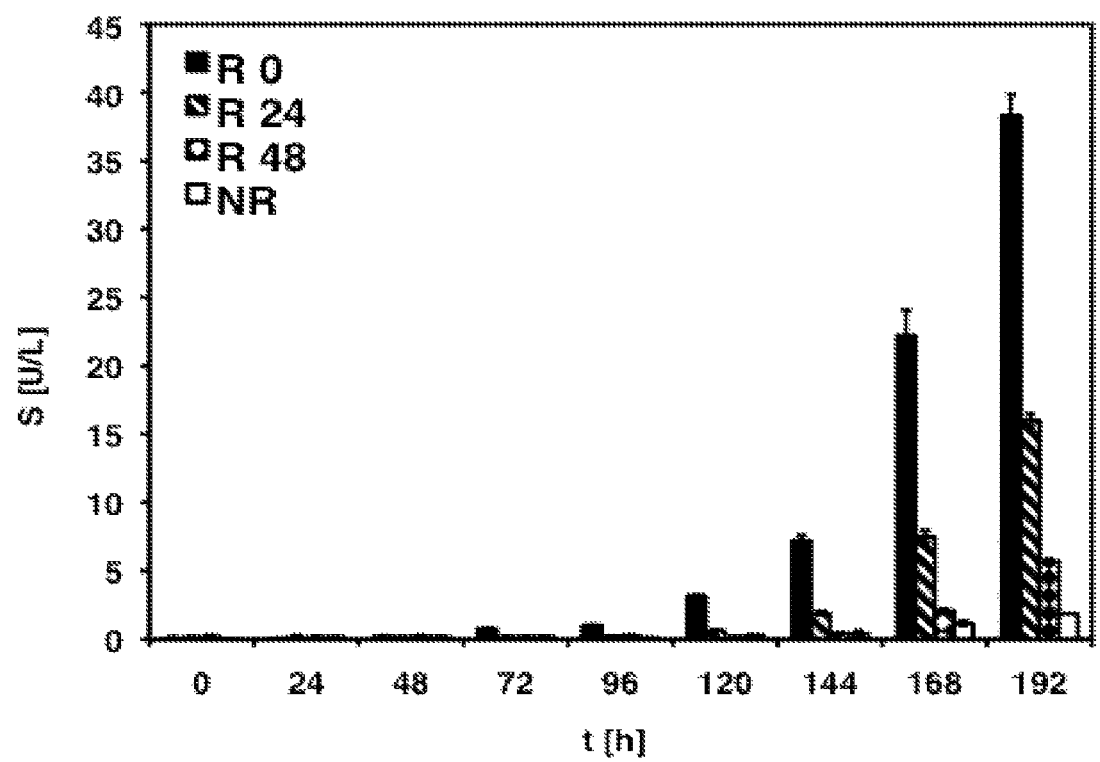

Capsule rupture was controlled by applying an external stimulus at a defined point in time, which leads to the induction of SecCell production and liberation of the compounds of interest at a later required time. Four groups of identical capsules, containing HEK-301$_9$ ($5 \times 10^5$ cells/ml of CS) and CHO-SEAP$_{18}$ ($2.5 \times 10^5$ cells/ml of CS), were cultivated with SecCell expression de-repressed sequentially by DOX removal either (i) immediately after (group 1), (ii) 24 hours after (group 2) or (iii) 48 hours after encapsulation and seeding (group 3). Group 4 was cultivated in the continued presence of doxycycline and served as a baseline to illustrate the tightness of the system. The cumulative SEAP activity of the supernatants of the four groups was monitored for six days (FIG. 4A). An increase in supernatant SEAP activity reflected the induction time frame of the respective capsule population and demonstrated timely controlled induction of capsule rupture.

Figure 4B:
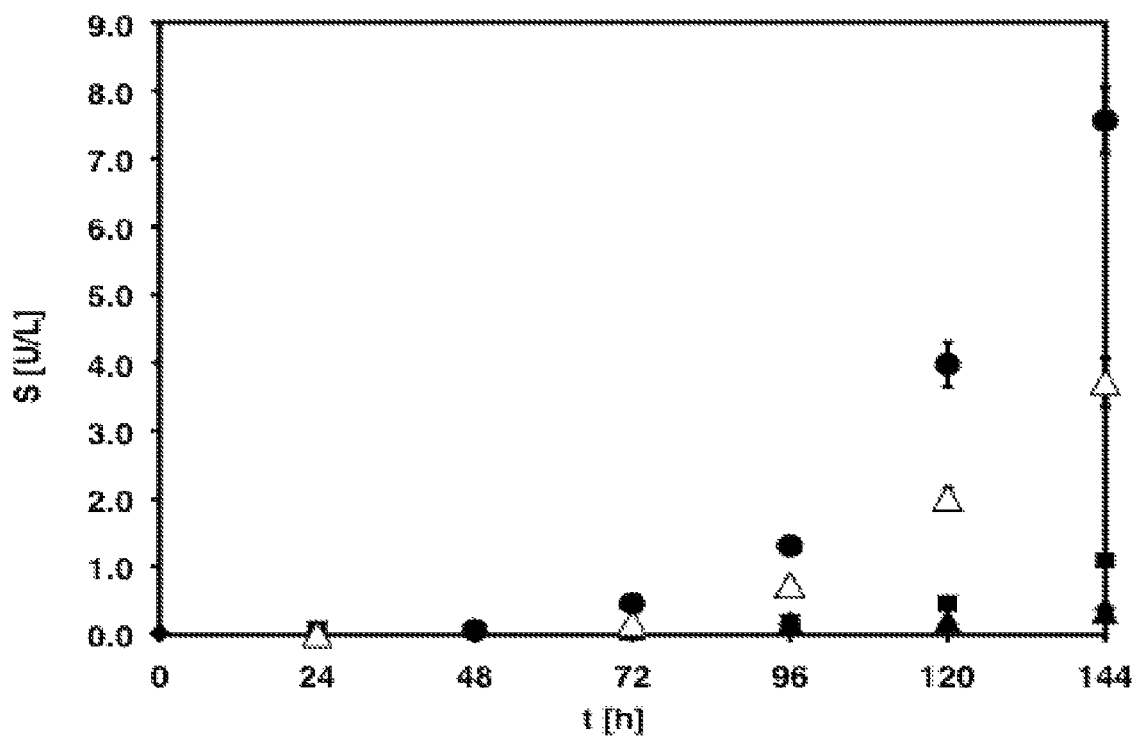

Another option to control the time of release is the titration of SecCell expression by using different DOX concentrations. Capsules containing HEK-301$_9$ ($5 \times 10^5$ cells/ml of CS) and CHO-SEAP$_{18}$ ($2.5 \times 10^5$ cells/ml of CS) were seeded into a 24-well plate and incubated with 0, 0.1, 0.5, 2, and 20 ng/ml DOX. Again, the cumulative SEAP activity of the supernatants was scored for 6 days. Capsule rupture and SEAP accumulation in the supernatant took progressively longer as DOX concentrations increased (from 0 ng/ml to 2 ng/ml). For the two highest DOX concentrations (2 ng/ml and 20 ng/ml), SEAP readings in the supernatant dropped to background levels indicating full repression of SecCell expression (FIG. 4B).

Figure 4C:
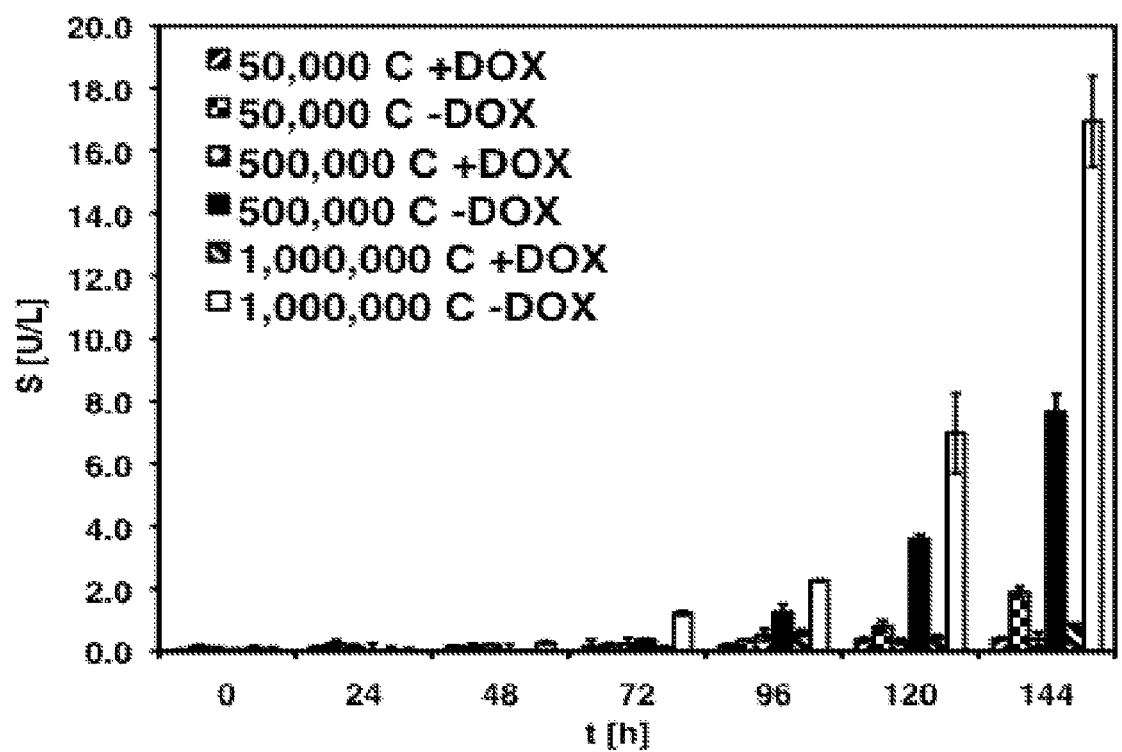

As a third option to control SecCell-mediated protein release from cellulose sulfate/pDADMAC capsules, the numbers of HEK-301$_9$ responder cells ($5 \times 10^4$/ml of CS, $5 \times 10^5$/ml of CS and $1 \times 10^6$/ml of CS) co-encapsulated with a constant amount of CHO-SEAP$_{18}$ (2.5×10$^5$ cells/ml of CS) were varied. SEAP accumulation profiles were again compared in repressed (+DOX) and induced (−DOX) SecCell expression states for six days (FIG. 4C). Encapsulation of higher numbers of the responder cell line HEK-301$_9$ lead to a quicker response to the stimulus, but also slightly increased the overall leakiness of the system possibly due to capsule rupture as a result of leaky cellulase expression from the tetracycline-responsive promoter.

Co-Cultivation of Different Capsule Populations

For various applications such as a single-shot vaccine or temporally spaced treatments it was demonstrated that it is possible to deliver a mixed capsule population and to release the compounds of interest at different points in time by inducing release with different triggering compounds. The capacity of the system to control the release of different molecules after inducing capsule rupture by two different antibiotics was investigated. HEK-301$_9$ (5×10$^5$ cells/ml of CS) together with CHO-SEAP$_{18}$ (2.5×10$^5$ cells/ml of CS) were encapsulated for one capsule population, and HEK-260$_{11}$(0.75×10$^5$ cells/ml of CS) engineered for macrolide-responsive SecCell expression together with IgG-producing CHO-B13-24 cells (5×10$^5$ cells/ml of CS) were encapsulated as the second capsule population. The two populations were mixed in a 1:1 ratio and incubated under various antibiotic conditions. To distinguish the two capsule populations in the mixture the HEK-301$_9$/CHO-SEAP$_{18}$-containing capsules were stained with FITC-dextran (150 kDa) whereas the HEK-260$_{11}$/CHO-B13-24-containing capsules were stained with tetramethyl-rhodamine isothiocyanate (TRITC, 150 kDa). The mixed capsule populations were seeded into four different groups which were incubated in the absence or presence of one or both antibiotics (DOX and EM) for five days. Accumulated SEAP and anti CD-18 antibody were measured in the culture supernatants after 5 days (FIG. 5). SEAP and IgG levels indicated that the respective release from the capsules was entirely controlled by the presence or absence of either antibiotic. Exclusive rupture of one capsule population did not appear to influence the other one since SecCell can only degrade capsules internally. Capsule integrity was also analyzed by microscopy 5 days after incubation. Bright-field and fluorescence micrographs showed exclusive rupture of capsule populations harboring cells with induced SecCell and confirmed the integrity of capsules containing HEK-301$_9$ or HEK-260$_{11}$ with repressed SecCell.

In Vivo Release of a Model Glycoprotein Upon Withdrawal of Doxycycline

Figure 6A:
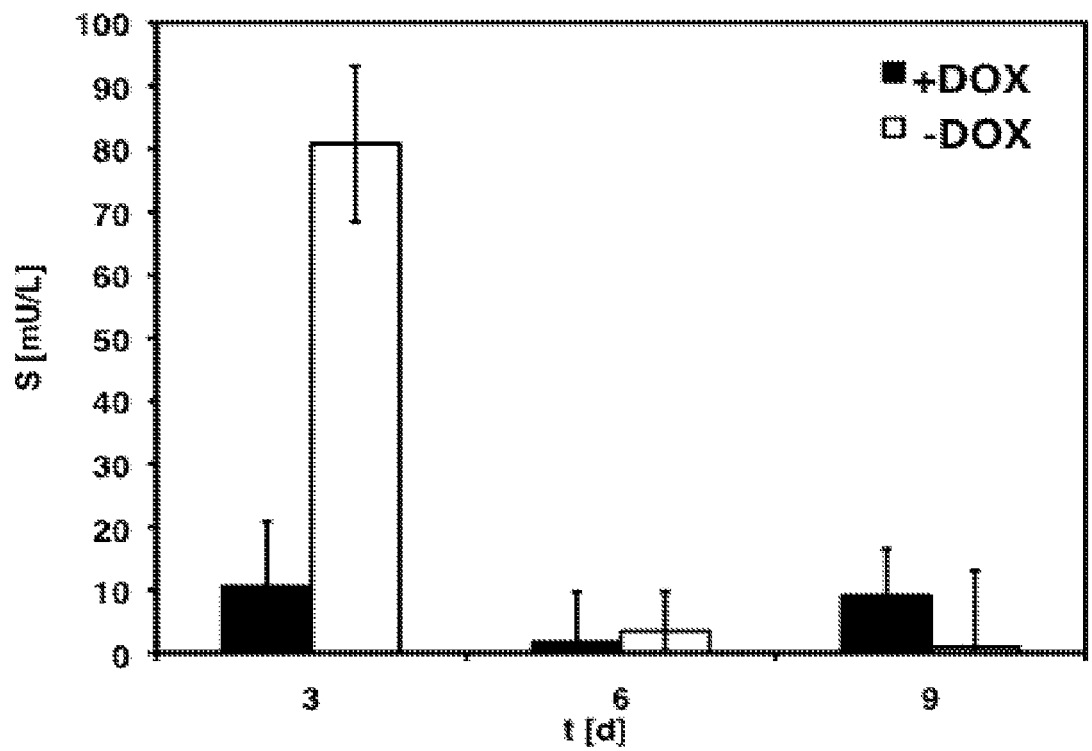
Figure 6B:
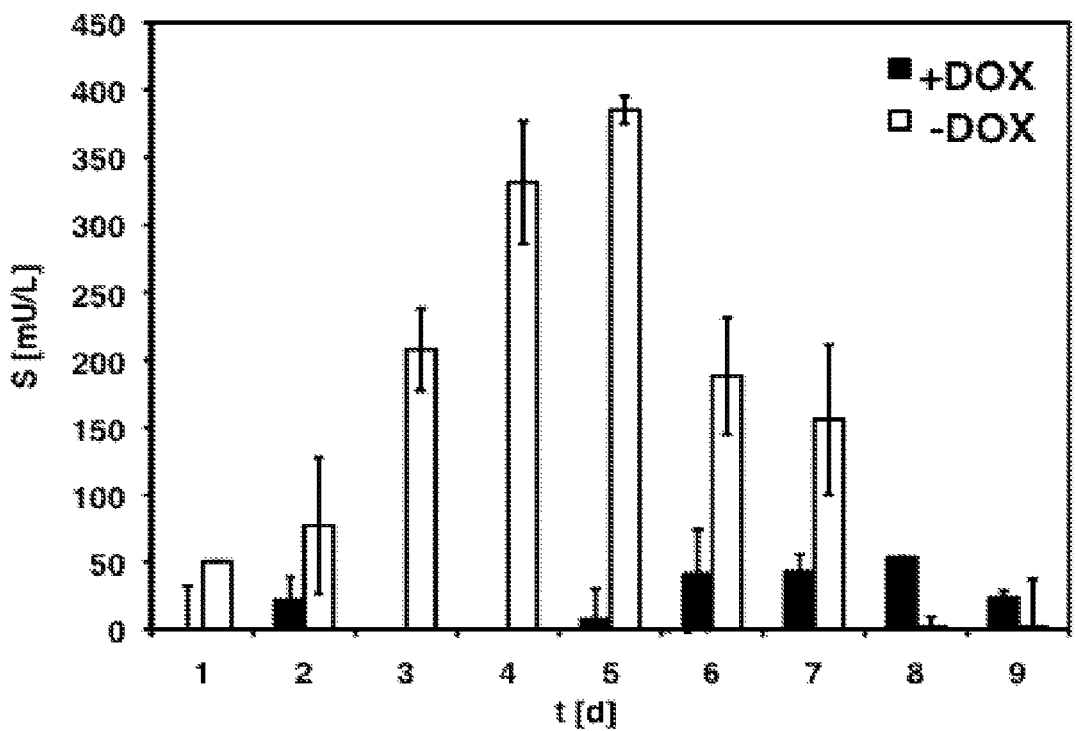

Capsules containing HEK-301$_9$ (5×10$^5$ cells/ml of CS), transgenic for doxycycline-responsive SecCell expression, and 100 µl SEAP (2 U/ml) concentrated from serum free CHO-SEAP$_{18}$ supernatants were injected intraperitoneally into two groups of mice. One group was given daily doxycycline injections (+DOX) to maintain the capsule system in a repressed state, whereas the second group was left untreated to induce capsule rupture (FIG. 6A). Parallel to the in vivo experiment, the same capsule populations were cultivated in the presence and absence of DOX in petri dishes and release profiles were compared to the in vivo situation (FIG. 6B).

Artificial insemination (AI) is the prime reproduction technology in modern stock farming. The precise determination of the estrus strongly influences the success rate of AI. Additionally, the in utero retrograde transport and leucocyte mediated phagocytosis reduce the lifetime of inseminated sperm and limit the fertilization potential window to approximately 20 hours. It was recently shown that high-throughput microencapsulation of bovine spermatozoa is compatible with standard cryopreservation procedures and proposed that encapsulation of sperm may prolong the fertilization period [Weber W, Rimann M, Schafroth T, Witschi U, Fussenegger M, J Biotechnol 2006; 123:155-63].

A novel bovine responsive gene expression system able to degrade CS/pDADMAC or CS-CMC-pDADMAC microcapsules in response to the pituitary luteinizing hormone has been established. In mammals luteinizing hormone (LH) is strongly expressed only in the late follicular phase and induces ovulation. However, during the luteal phase and in the early follicular phase only low levels of luteinizing hormone can be detected. Therefore it is a highly specific signal marking the time of ovulation. Rat luteinizing hormone receptor (rLHR) and bovine luteinizing hormone receptor (bLHR) were functionally expressed in human endothelial kidney cells to detect bovine luteinizing hormone (bLH). The functionality of the expressed receptors was demonstrated by assaying intracellular cAMP levels. HEK293T cells transiently transfected for rLHR or bLHR expression actively responded to bLH by increasing the intracellular cAMP levels whereas in the absence of bLH the cells retained basal concentrations of cAMP (FIG. 7). Interestingly, cells expressing rLHR showed a stronger cAMP response than bLHR expressing cells.

To convert the bLH-mediated cAMP-signal from the activated LHR into a gene expression system a variant of the CREB1-inducible promoter was used. The LHR-signaling activates the protein kinase A pathway triggering the phosphorylation of various transcription factors like CREB1. Phosporylated CREB1 translocates into the nucleus and activates gene expression from CRE-box containing promoters. By utilizing luciferase as reporter gene a LHR-signal dependent activation of gene expression from P$_{CRE}$ was demonstrated (FIG. 8). Quantification of P$_{CRE}$ controlled gene expression over time demonstrated a time-dependent and bLH-dose dependent expression of SEAP (FIG. 9). A stronger bLH-dependent activation of rLHR over bLHR was found. By comparing the cAMP response and the reporter gene expression of bLHR and rLHR-expressing HEK293T cells the results clearly demonstrate the stronger bLH-dependent rLHR activation. A higher binding affinity of the rLHR to bLH results in a stronger receptor interaction and activation followed by a corresponding increases in intracellular cAMP.

A HEK293T-derived cell line engineered for stable expression of rLHR was established (FIG. 10). Encapsulation of cells engineered for constitutive rLHR expression and transfected for P$_{CRE}$-dependent reporter gene expression revealed that bLH was able to penetrate CS/pDADMAC capsules (FIG. 11). Cells enclosed by microcapsules remained viable, proliferated and actively responded to bLH as measured by reporter gene expression. A time-independent increase in SEAP expression induced by bLH-dependent rLHR-signaling was demonstrated.

CK04 cells constitutively expressing rLHR show a steady increase in reporter gene expression after the receptor activation. The time-independent LHR-activation may be based on the constitutive promoter (P$_{hCMV}$) controlling the receptor expression. A P$_{hCMV}$ controlled LHR-expression is not subject to native LHR transcriptional down regulation because it lacks the response elements of the native LHR-promoter.

By replacing the reporter genes with an engineered secreted cellulase a bLH-dependent cellulase expression was confirmed by western blot analysis and cellulase activity assays (FIG. 12). Encapsulation of CK04 cells transiently transfected for P$_{CRE}$ dependent cellulase expression resulted in a bLH-induced CS/pDADMAC microcapsule degradation (FIG. 13). However, in the absence of bLH the capsules remained intact. For an in vivo application in cattle the amount of the inducer is specified to the pre-ovulatory LH-concentration. The microcapsule degradation properties can therefore not be changed by simply changing the inducer concentration. In the experimental setup $1\times10^6$ cells per mL were encapsulated in a CS-solution. Induction of these encapsulated cells resulted in a strong capsule degradation after 24 hours. For specific applications the time of degradation may be altered by varying the amount of encapsulated cells and/or the concentration of CS in the encapsulation process.

A particular example of a construct useful for luteinizing hormone regulation is as follows:

Expression of Functional LHRs in HEK293T Cells

Full-length cDNAs encoding the LHRs of rat (r) and bovine (b) origin were cloned under control of the strong constitutive human cytomegalovirus promoter ($P_{CMV}$) as previously described [Kawate N, Tamada H, Inaba T, Sawada T, Journal of Reproduction and Development 2002; 48:8; Ulaner G A, Chuang J, Lin W, Woodbury D, Myers R V, Moyle W R, J Endocrinol 1999; 163:289-97]. The expression vectors were transiently transfected into HEK293T cells. The functionality of the expressed LHRs was determined 48 hours post-transfection by assaying the intracellular cAMP increase in response to the presence of bLH (FIG. 7). The bLH-induced LHR-signaling activates the protein kinase A pathway and therefore stimulates adenylyl cylcase-dependent cAMP production [Cooke B A, Mol Cell Endocrinol 1999; 151:25-35; Seger R, Hanoch T, Rosenberg R, Dantes A, Merz W E, Strauss J F $3^{rd}$, Amsterdam A, J Biol Chem 2001; 276:13957-64]. The expression of bLHR resulted in a 12-fold increase in intracellular cAMP-level in the presence of bLH 1 hour post-induction whereas the non-induced cells retained basal levels. However, when the rLHR was expressed the detected cAMP-level increased to 29-fold level of the non-induced cells.

Identification of a LHR-Signaling Inducible Promoter

Functional expression of LHRs on the cell surface results in the stimulation of PKA and an increase of intracellular cAMP in response to bLH. It was evaluated whether the activated LHR-signaling may induce a PKA-responsive promoter. A version of the cAMP-responsive element binding protein 1 (CREB1) inducible promoter, carrying a cAMP response element (CRE) immediately upstream of a TATA-like promoter, was tested for its response to rLHR-signaling. Transient cotransfection experiments of pLEN-rLHR and pCRE-Luc revealed a 10-fold induction of luciferase expression when the rLHR was activated by bLH (Figure). The luciferase reporter gene was exchanged to SEAP to evaluate the time-dependent activation characteristics of $P_{CRE}$ by LHR-signaling. HEK293T cells were transiently cotransfected with (i) pLEN-rLHR and pCK62 (pCK62, $P_{CRE}$-SEAP-pA) (ii) pcDNA3.1-bLHR and pCK62 or (iii) pcDNA3.1(+) and pCK62 as control. 24 hours post-transfection the cells were induced by bLH and the SEAP expression was determined over time. The expression of either LHR-variant resulted in a bLH-induced LHR-signaling leading to a permanent increase in SEAP expression, whereas non-induced cells remained basal SEAP-levels (FIG. 9). Control cells transfected with the empty expression vector showed only basal SEAP levels in the absence and presence of bLH. In comparing rLHR- and bLHR-expressing cells a 3-fold increase in maximal SEAP expression in response to bLH of the rLHR over the bLHR was detected. This confirms an increased activation of the intracellular cAMP production in the presence of functional rLHR. Therefore further experiments were only performed with cells expressing the rLHR. A stable HEK293T-derived cell line transgenic for constitutive expression of rLHR (CK04) was generated. After clonal expansion several clones were transiently transfected for $P_{CRE}$-controlled luciferase expression and screened for their performance (FIG. 10). In response to bLH clone number 6 showed the highest performance based on functional stable expression of the rLHR, showing a 17.0±0.2 fold induction of luciferase expression. This stable cell line was used to perform all remaining experiments.

Bovine Luteinizing Hormone can Penetrate CS/pDADMAC-Capsules

To determine whether bLH can penetrate microcapsules and activate the gene expression of encapsulated cells, CK04 cells were transiently transfected with a vector encoding $P_{CRE}$ controlled eYFP expression (pCK91, $P_{CRE}$-eYFP-pA). After transfection the cells were encapsulated in CS/pDADMAC-microcapsules and cultured in the absence or presence of bLH. When bLH was present the eYFP expression of encapsulated cells was strongly induced resulting in bright fluorescent cells. In contrast in the absence of bLH the cells remained non-fluorescent. Light microscopic monitoring further revealed that the cells were actively growing and that cell clusters were formed inside the capsules. It was also investigated if the activation of encapsulated cells is bLH dose- and time-dependent. Therefore, CK04 cells transiently transfected for $P_{CRE}$ dependent SEAP expression (pCK62, $P_{CRE}$-SEAP-PA) were encapsulated, the capsules cultured in the absence or presence of 100 ng/ml or 500 ng/ml bLH and the SEAP expression measured in 12 hours intervals (FIG. 11). It was proven that bLH can penetrate the microcapsules, and a steady increase of SEAP-levels over time is demonstrated. Additionally, the experiments revealed a bLH-dose dependent SEAP expression. 60 hours post-induction a 2.3±0.2 fold higher SEAP expression for LH-surge doses of bLH compared to 100 ng/ml hormone was measured. The steadily increasing SEAP levels further indicate the survival of cells inside the capsules.

bLH Controlled Expression of β-1.4-Glucanase May Disrupt CS-Microcapsules

A novel bLH-responsive microcapsule degradation system was established by placing an engineered secreted version of the lytic enzyme endo-1.4-beta-glucanase gene (cellulase) under control of $P_{CRE}$. The bLH-induced expression of secreted cellulase was demonstrated in CK04 cells stably expressing rLHR after transient transfection for $P_{CRE}$ controlled cellulase expression (pCK71, $P_{CRE}$-cellulase-pA) by western blot analysis and cellulase activity assay. The specific immunohistochemical detection revealed a strong cellulase expression in the presence of bLH, whereas non-induced cells showed only low basal expression. The protein had the estimated size of 57 kDa. Additionally, the functionality of the pCK71-encoded cellulase was evaluated by performing a cellulase activity assay (FIG. 12). An 8.4±0.2 fold increase in cellulase activity in bLH-induced CK04 cells transiently transfected with pCK71 was demonstrated.

To evaluate the effect of bLH-induced cellulase expression on microcapsules, CK04 cells transiently transfected for $P_{CRE}$ controlled cellulase expression (pCK71, $P_{CRE}$-cellulase-pA) were encapsulated. Time course experiments revealed a bLH-dependent capsule degradation in vitro (FIG. 13a). When bLH was present the bLH-LHR signaling of the encapsulated cells resulted in an expression of cellulase followed by a disruption of microcapsules by cleaving the β-1.4-glycosidic bonds of the CS-microcapsule matrix. However, in the absence of bLH the microcapsules remained intact, indicating that the basal expression of the cellulase does not affect the capsule integrity. In the presence of bLH the quantification of the capsule degradation resulted in 98% rate of disrupted capsules 24 hours post-induction (FIG. 13b). However, in the absence of bLH only 6% of the microcapsules collapsed spontaneously. The results indicate that the capsule disruption is strongly dependent on the bLH-dependent expression of cellulase.

Co-Expression of Annexins

Oviductal sperm reservoirs are widespread in mammals. The sperms are binding to surface receptors of the epithelium in the oviductal tract near the site of fertilization which prolongs the sperm lifespan by inhibiting capacitation, therefore preserving the sperm in a fertile state, and by reducing the incidence of polyspermy. Annexins are putative oviductal receptors for bovine sperm binding but the direct sperm interaction is accounted for fucosyl-residues (Ignotz G G, Cho M Y, Suarez S S, Biol Reprod 2007; 77:906-13).

CHO-K1 and HEK-293 cells are co-transfected with bovine fucosyltransferase and/or either Annexin A1 or Annexin A5. The expression of these surface receptors results in the binding of sperms to the cell surfaces and the formation of sperm clusters. However, the co-expression of bovine alpha-1.3-fucosyl-transferase with either Annexin A1 or 5 does not influence the sperm binding ability. Additionally, the sperm binding to cell surface receptors prolongs the sperm survival in in vitro experiments.

EXAMPLES

Abbreviations

BF, bright field;
bLH, bovine luteinizing hormone
bLHR, bovine luteinizing hormone receptor;
cellulase, engineered version of β-1.4-endoglucanase gene from *Bacillus subtilis*;
CS, cellulose sulphate;
DOX, doxycycline;
ET1, erythromycin-dependent transactivator;
eyFP, enhanced yellow fluorescent protein;
FITC, fluorescein isohiocyanate;
luciferase, firefly luciferase gene from *Photinus pyralis*;
pA, polyadenylation signal;
$pA_{hgh}$, polyadenylation signal of the human growth hormone;
$pA_{SV40}$, polyadenylation signal of the simian virus 40;
$P_{CRE}$, CREB1 responsive TATA-like promoter;
$P_{ETR}$, macrolide responsive promoter;
$P_{hCMV}$, human cytomegalovirus immediate early promoter;
$P_{hCMV*-1}$, tetracycline-responsive promoter;
$P_{SV40}$, simian virus 40 promoter;
rLHR, rat luteinizing hormone receptor;
SEAP, human placental secreted alkaline phosphatase;
$SS_{Igk}$, signal sequence derived from the murine Igκ-chain V-12-C region;
$T_{myc}$ protein tag encoding a c-myc epitope.
TRITC, tetramethylrhodamine isothiocyanate.
tTA, tetracycline-dependent transactivator;
ZeoR, Zeocin resistance gene.

1) Vector Design pAAV-MCS ($P_{hCMV}$-Intron$_{b-globin}$-pA$_{hGH}$) [Stratagene, La Jolla, Calif., USA],
pEF4-MycHisA ($P_{hEF1α}$-MCS-T$_{MYC}$-T$_{HIS}$-pA$_{bGH}$), pcDNA3.1(+) (cloning vector) and pZeoSV2(+) ($P_{CMV}$-ZeoR-pA) [Invitrogen, Carlsbad, Calif., USA],
pIRESbleo ($P_{hCMV}$-MCS-Intron$_{synthetic}$-IRES$_{EMCV}$-Bleo-pA$_{bGH}$), pPur ($P_{SV40}$-Puro-pA$_{SV40}$), pSEAP2-control ($P_{SV40}$-MCS-SEAP-pA$_{SV40}$-E$_{SV40}$; E$_{SV40}$, enhancer of SV40 virus), pCRE-Luc ($P_{CRE}$-luciferase-pA) [Clontech, Palo Alto, Calif., USA],
pDF51 ($P_{hCMV}$-Intron$_{b-globin}$-ET1-pA$_{hGH}$), pDF60 ($P_{CMV}$-eYFP-pA), pDF75 ($P_{ETR}$-SEAP-IRES$_{PV}$-ET1-pA$_{SV40}$) and pDF109 ($P_{hCMV}$-Intron$_{b-globin}$-SEAP-pA$_{hGH}$) [Fluri D A, Baba M D, Fussenegger M, BMC biotechnology 2007; 7:75],
pDF191 ($P_{hEF1α}$-SeXy-pA$_{bGH}$) [Fluri D A, Kelm J M, Lesage G, Baba M D, Fussenegger M, Biotechnology and bioengineering 2007; 98(3):655-67],
pMF111 ($P_{hCMV*-1}$-SEAP-pA$_{SV40}$) and pSAM200 ($P_{SV40}$-tTA-pA$_{SV40}$) [Fussenegger M, Moser S, Mazur X, Bailey J E, Biotechnology progress 1997; 13(6):733-40],
pMF172 ($P_{PIR}$-SEAP-pA$_{SV40}$) [Fussenegger M, Morris R P, Fux C, Rimann M, von Stockar B, Thompson C J, Bailey J E, Nature biotechnology 2000; 18(11):1203-8],
pWW35 ($P_{SV40}$-ET1-pA$_{SV40}$) [Weber W, Fux C, Daoud-el Baba M, Keller B, Weber C C, Kramer B P, Heinzen C, Aubel D, Bailey J E, Fussenegger M, Nature biotechnology 2002; 20(9):901-7],
pcDNA3.1-bLHR ($P_{CMV}$-bLHR-pA) [Kawate N, Tamada H, Inaba T, Sawada T, Journal of Reproduction and Development 2002; 48:8], and
pLEN-rLHR ($P_{CMV}$-rLHR-pA) [Ulaner G A, Chuang J, Lin W, Woodbury D, Myers R V, Moyle W R, J Endocrinol 1999; 163:289-97]
have been described previously.

The cellulase of *Bacillus subtilis* 168 (GenBank accession no.: AY044252) was PCR-amplified from genomic DNA using oligonucleotides ODF67: (5'-CG GGATCCACCATGGA GACAGACACACTCCTGC-TATGGGTACTGCTGCTCTGGGTTCCAG-GTTCCACTGGTGA CGCAGGGACAAAAACGCCAG-TAGCC, SEQ ID NO:1; BamHI, underlined; start codon in italics) and ODF68: (5'-GGAATTCTCA TCTAGAATTTGGTTCTGTTCCCCAAAT, SEQ ID NO:2; EcoRI and XbaI, underlined), restricted with BamHI/XbaI and cloned into the corresponding sites (BamHI/XbaI) of pEF4-MycHisA (pDF195 [$P_{hEF1α}$-SecCell-pA$_{bGH}$]).

This fused the cellulase 5' to the signal sequence derived from the murine Igκ-chain V-12-C region ($SS_{Igk}$) replacing the first 115 nucleotides of the open reading frame and 3' to the Myc tag ($T_{MYC}$) which resulted in a secreted cellulase (SecCell; $SS_{Igk}$-CELLULASE-$T_{MYC}$). SecCell was excised from pDF195 by BamHI/PmeI and cloned into the compatible sites (BamHI/HincII) of pAAV-MCS resulting in pDF196 ($P_{hCMV}$-Intron$_{b-globin}$-SecCell-pA$_{hGH}$).

pDF260 ($P_{ETR}$-SecCell-pA$_{hGH}$) was assembled by restricting pDF196 with ClaI/BglII and ligating SecCell into the corresponding sites (ClaI/BglII) of pDF85 ($P_{ETR}$-Intron$_{b-globin}$-SEAP-pA$_{hGH}$). pDF85 had been constructed by excising $P_{ETR}$ from pDF75 with BssHII/NruI and cloning the insert into the MluI/BsaBI sites of pDF109. pDF301 ($P_{hCMV*-1}$-SecCell-pA$_{SV40}$) was constructed by a multistep cloning procedure including (i) excision of SecCell from pDF196 using EcoRI/XhoI, (ii) subcloning (EcoRI/XhoI) into pMF172 resulting in pDF300 ($P_{PIR}$-SecCell-pA$_{SV40}$) and (iii) excising SecCell from pDF300 with SpeI/HindIII and cloning the fragment into the compatible sites (XbaI/HindIII) of pMF111. pDF323 ($P_{hCMV}$-ET1-Intron$_{synthetic}$-IRES$_{EMCV}$-Bleo-pA$_{bGH}$ was assembled by excising ET1 from pDF51 (EcoRI/BglII) and inserting it (EcoRI/BamHI) into pIRESbleo.

PCK62, a vector encoding $P_{CRE}$ driven SEAP expression ($P_{CRE}$-SEAP-pA), was obtained by PCR-amplification of $P_{CRE}$ from pCRE-Luc using oCK52: 5'-ggggtaccaggcct-gagctCTTATCATGTCTGGATCAGC-3', SEQ ID NO:3, and oCK53: 5'-ggaattccatggatcgaTATATAC CCTCTA-GAGTCTCC-3', SEQ ID NO:4 and introduction into pSEAP2_basic (KpnI/EcoRI).

pCK71, a vector encoding $P_{CRE}$ driven cellulase expression ($P_{CRE}$-cellulase-pA), was obtained by PCR-amplification of cellulase from pDF260 using oCK70: 5'-gactagtggg-tata tagatctaagcttgaatTCCACCATGGAGACAGACACAC-3', SEQ ID NO:5 and oCK71: 5'-gctctagatcaagcgtaatct-ggaacatcgtatgggtaATTTGGTTCTGTTCCCCAAATCAG-3', SEQ ID NO:6, and introduction into pCRE-Luc (HindIII/XbaI).

pCK 90, a vector encoding promoter-less eYFP (eYFP-pA), was obtained by PCR amplification of eYFP from pDF60 using oCK86: 5'-gctctagaTTACTTGTA-CAGCTCGTCC ATGC-3', SEQ ID NO:7, and oCK87: 5'-ggaattccaagcttCCACCATGGTGAGCAAGGGC-3', SEQ ID NO:8, and cloning into pSEAP2_basic (EcoRI/XbaI).

PCK91, a vector encoding $P_{CRE}$ driven eYFP expression ($P_{CRE}$-eYFP-pA), was obtained by introduction of $P_{CRE}$ from pCRE-Luc (Clontech) into pCK90 (NotI/HindIII).

2) Constructs Useful for Erythromycin and Doxycycline Regulation

Cell Culture, Transfection and Construction of Stable Cell Lines

Human embryonic kidney cells, transgenic for the adenovirus type 5-derived E1 region and the simian virus 40 (SV40) large T-antigen (HEK293-T; [Mitta B, Rimann M, Ehrengruber M U, Ehrbar M, Djonov V, Kelm J, Fussenegger M, Nucleic Acids Res 2002; 30(21):e113]), human fibrosarcoma cells (HT-1080; ATCC CCL-121), human cervical carcinoma cells (HeLa; ATCC CCL-2), baby hamster kidney cells (BHK-21, ATCC CCL-10) and all HEK293-T derivatives (HEK-ET1$_5$, HEK-tTA$_2$, HEK-DF260$_{11}$, HEK-DF301$_9$) were cultivated in Dulbecco's modified Eagle's medium (DMEM, Invitrogen, Carlsbad, Calif., USA) supplemented with 10% fetal calf serum (FCS; PAN Biotech GmbH, Aidenbach, Germany; cat. no. 3302-P251110, lot no. P251110) and 1% penicillin/streptomycin solution (Sigma Chemicals, St. Louis, Mo., USA). Chinese hamster ovary cells (CHO-K1; ATCC CCL-61; CHO-B13-24; ATCC CRL-11397) and the CHO-K1 derivative CHO-SEAP$_{18}$ (see below) were cultivated in ChoMaster® HTS medium (Cell Culture Technologies GmbH, Gravesano, Switzerland) supplemented with 5% FCS and 1% penicillin/streptomycin solution. HEK-ET1$_5$ was created by transfecting pDF323 into HEK293-T and selecting for two weeks using 100 µg/ml zeocin (Invitrogen) before clonal selection in 96-well plates. HEK-tTA$_2$ was engineered by co-transfecting pSAM200 and pIRES-bleo into HEK293-T and selection using 100 µg/ml zeocin for two weeks before clonal selection in 96-well plates. HEK-260$_{11}$ was created by co-transfecting pDF260 and pPur into HEK-ET1$_5$ and subsequent selection for two weeks using 1 µg/ml puromycin. HEK-301$_9$ was engineered by co-transfecting pDF301 and pPur into HEK-tTA$_2$ before selection for two weeks using puromycin (Calbiochem, San Diego, Calif., USA). Both HEK-260$_{11}$ and HEK-301$_9$ were screened clonally in 96-well plates for optimal regulation performance. CHO-SEAP$_{18}$ was obtained by co-transfecting pPur and pSEAP2-control (Clontech) into CHO-K1 followed by selection for two weeks in medium containing 10 mg/ml puromycin and screening for maximum human placental secreted alkaline phosphatase (SEAP) expression.

Capsules containing cells were cultivated in mixed medium consisting of 50% DMEM (Invitrogen) and 50% HTS (Cell Culture Technologies GmbH) supplemented with 7.5% FCS (PAN biotech GmbH).

Chemicals Used for Transgene Regulation

For all in vitro experiments, erythromycin (Sigma, E-5289) was dissolved in ethanol and used at a final concentration of 1 mg/ml. Doxycycline (Sigma, D-9891) was dissolved in PBS and used at a final concentration of 1 mg/ml for in vitro experiments and at a final concentration of 25 mg/kg for in vivo experiments.

Quantification of Cellulase, SEAP and Antibodies

Cellulase was quantified using EnzCheck® fluorescent substrate (Molecular Probes, Eugene, Oreg., USA) according to the manufacturer's protocol: 20 µl of cell culture supernatant was centrifuged at 16,000×g for one minute to remove cell debris and 15 µl of appropriate dilutions in PBS (Invitrogen, cat. no. 21600-069) were transferred to a 384-well plate containing 15 µl sodium acetate buffer (200 mM sodium acetate, pH 5.5) per well supplemented with 3 µl substrate solution. Plates were incubated at 37° C. for 30 minutes and fluorescence intensity was measured subsequently at 340 nm (excitation wavelength) and 450 nm (emission wavelength) in a Genios Pro multiwell plate reader (Tecan A G, Maennedorf, Switzerland). Absolute cellulase levels were determined by comparing the fluorescence intensities to readings of standardized solutions containing known concentrations of *Aspergillus niger* cellulase (Sigma, cat. no. 22178). Quantification of human placental secreted alkaline phosphatase (SEAP) in the supernatant of microencapsulated cells or in mouse serum was performed as described previously [Berger J, Hauber J, Hauber R, Geiger R, Cullen B R, Gene 1988; 66(1):1-10]. Anti CD18 IgG was quantified using a standard sandwich ELISA. In brief, high protein-binding 96-well plates (Corning, N.Y., USA) were coated overnight with Fc-specific anti-human IgG (Sigma, cat. no. 12136, lot no. 105K4774) before blocking for 2 hours with 1% BSA in PBS (Invitrogen). Diluted culture supernatants were added to individual wells, incubated for 2 hours at 4° C. before washing three times with 200 ml PBS containing 0.02% Tween and adding a secondary peroxidase-coupled anti-human IgG (Sigma, cat. no. A0170, lot no. 026K4784). After another three washing steps, chromogenic tetramethyl benzidine (TMB) substrate (Interchim, Montluçon, France) was added and the reaction was stopped after 10 minutes by adding 50 ml/well of 1M $H_2SO_4$ before measuring absorbance at 450 nm in a multi-well plate reader (TECAN). Absolute antibody levels were determined by comparing absorbance readings to those for purified IgG antibody standard (Gammanorm®, Octapharma GmbH, Langenfeld, Germany).

Encapsulation

Cells were encapsulated using the Inotech Encapsulator IE-50R (Inotech Biotechnologies Ltd., Basel, Switzerland) according to the manufacturer's protocol at the following settings: 0.2 mm nozzle, 20 ml syringe at a flow rate of 410 units, a nozzle vibration frequency of $1250 s^{-1}$ and $1150 V$ for bead dispersion. Cellulose sulfate (CS, Euroferm GmbH, Erlangen, Germany, batch no. FCY-71) was dissolved to 2% (w/v) in PBS and stirred for 16 hours. The precipitation solution consisted of 1% (w/v) poly-diallyl-dimethyl-ammonium chloride (pDADMAC, Euroferm) in PBS containing 0.0002% Tween-20. For encapsulation, the cells, proteins or fluorescently labeled molecules were re-suspended at desired concentrations in CS and transferred to a syringe before injecting the solution into the encapsulator which generated CS droplets and sprayed them into the agitated precipitation solution where product-containing CS-pDADMAC capsules formed. After hardening of the CS-pDADMAC capsules, the precipitation solution was exchanged with PBS and the capsules were incubated in tissue culture plates at 37° C. and 5% $CO_2$ in a humidified atmosphere.

Capsule Formation with Varying Amounts of Sodium Cellulose Sulphate (NaCS)/Carboxymethyl-Cellulose (CMC)

All values are given in weight per volume (w/v). Microcapsules composed of various chemical compositions were produced and properties compared by dissolving (i) 2% NaCS, (ii) 1.8% NaCS and 0.2% CMC, (iii) 1.5% NaCS and 0.5% CMC or (iv) 2% CMC in phosphate buffered saline (PBS) over night. The microcapsules were formed by polymerization in a pDADMAC solution as described in the preceding paragraph using the automated Inotech Encapsulation protocol. With increasing CMC concentrations the microcapsules stability increases and the capsules are less transparent (FIG. 14A). Increasing CMC concentrations additionally enhance the stickiness of the capsules and result in a capsule cluster formation (FIG. 14B). However, in the absence of NaCS no intact capsules are formed.

Immunoblotting

Culture supernatants from transiently transfected HEK293-T were mixed with 5×SDS loading buffer (50% glycerol, 10% SDS, 250 mM Tris, pH 6.8 containing 10% (v/v) beta-mercaptoethanol) and boiled for five minutes before loading onto a 10% denaturing SDS-PAGE gel. Proteins were electroblotted onto polyvinylidene difluoride (PVDF) membranes (Millipore, Bedford, Mass., USA). After blocking in Tris buffered saline (TBS, 50 mM Tris, 150 mM NaCl, pH 7.5) containing 3% skimmed dry milk (Rapilait, Migros, Switzerland), the membranes were incubated with a primary antibody specific for the C-myc tag (Santa Cruz Biotechnology, Santa Cruz, Calif., USA; cat. no. SC-40, lot no. E2207). Specific bands were visualized using an anti-mouse IgG coupled to horseradish peroxidase (ECL™ anti-mouse IgGxHRP, Amersham, Buckinghamshire, UK; cat. no. NA931V, lot no. 357597) and a chemiluminescence-based assay (ECL™ plus, Amersham) according to the manufacturer's protocol.

Microscopy

Microscopic analysis and time-lapse movies were generated on a LEICA DMI-6000 microscope equipped with appropriate filters for eYFP, FITC and Cy3 detection, and a heated, humidified incubation chamber containing 5% $CO_2$.

Animal Studies

Female OF1 (oncins france souche 1) mice were obtained from Charles River Laboratories (Lyon, France). 700 ml of PBS solution containing 50% capsules was administered intraperitoneally to mice. A PBS solution containing DOX was injected every 24 hours. Blood samples were collected retroorbitally 3, 6 and 9 days after capsule injection. All experiments involving mice were performed according to the European Community Council directive (86/609/EEC), approved by the French Ministry of Agriculture and Fishery.

3) Constructs Useful for Luteinizing Hormone (LH) Regulation

Cell Culture, Transfection and Construction of Stable Cell Lines Expressing LHR

For DNA-transfection, $3\times10^5$ HEK293-T cells per well in a 6-well plate were seeded 24 h prior to transfection. 3 µg of total DNA (for cotransfections 2.5 µg LHR-expression construct and 0.5 µg reporter construct were used) in 100 µl 0.25 M $CaCl_2$ were mixed with 100 µl of $CaPO_4^{3-}$ solution (100 mM HEPES, 280 mM NaCl, 1.5 mM $Na_2HPO_4$, pH 7.1) and incubated for 15 min at room temperature (RT) to allow precipitate formation. The DNA-calcium phosphate precipitates were transferred to the cell culture and centrifuged onto the cells (5 min, 1200×g). Transfected cells were incubated for 3 h at 37° C. The cell medium was replaced by fresh medium and the cells were cultured in the absence or presence of 500 ng/ml bovine luteinizing hormone (bLH, National Hormone & Peptide program, CA, USA). For encapsulation $3\times10^6$ CK04 cells were seeded in a petri dish 24 h prior to transfection. DNA precipitates were prepared by mixing 10 µg of total DNA in 500 µl of 0.25 M $CaCl_2$ with 500 µl of $CaPO_4^{3-}$ and incubated for 15 min at RT to allow crystal formation. The DNA-precipitates were added to the cell culture and the cells were grown for 5 hours.

HEK293T cells transgenic for rLHR expression (CK04) were constructed by cotransfection of pLEN-rLHR and pZeoSV2(+) followed by clonal selection. Single clones were transiently transfected with pCRE-Luc (Stratagene) and assayed for their luciferase expression in the absence or presence of bLH.

Capsule Production and Capsule Disruption Experiments

Cells were encapsulated using the Inotech Encapsulator Research Unit IE-50R (Inotech Biotechnologies Ltd, Basel, Switzerland). CK04 semi-confluent cells were transiently transfected for bLH-dependent eYFP (pCK91, $P_{CRE}$-eYFP-pA), SEAP (pCK62, $P_{CRE}$-SEAP-pA) or cellulase (pCK71, $P_{CRE}$-cellulase-pA) expression. After transfection the cells were detached using trypsin (PAN Biotech GmbH, Aidenbach, Germany, Cat. No. P10023500) and collected in DMEM. The cells were counted using a Casy Counter (Scharfe Systems, Reutlingen, Germany) and $1\times10^6$ cells were resuspended in sodium cellulase sulfate solution (2% (w/v) in PBS, CS, Euroferm, Erlangen, Germany, Batch-No: FCY-06A) and aseptically encapsulated according to the standard protocol using the following settings: 0.2 mm nozzle with a nozzle vibration frequency of 1250 Hz, 20 ml syringe at a flow rate of 410 units, voltage for bead dispersion 1.15 kV. The CS-cell solution was dispersed into a 5% (v/v) poly-diallyl-dimethyl-ammonium chloride (pDADMAC) solution and incubated for 1 min for membrane hardening followed by 3 washing steps in PBS. The capsules were transferred into fresh DMEM supplemented with 10% (v/v) FCS and 1% (v/v) P/S and cultured at 37° C. in the absence or presence of bLH.

Quantification of Reporter Gene Expression

The intracellular cAMP production of cells was quantified using the cAMP Fluorescence Polarization (FP) Biotrak Immunoassay System (GE Healthcare Bio-Sciences GmbH, Otelfingen, Switzerland, Cat No. RPN3595) according to the manufacturer's protocol. The expression of firefly luciferase was determined with the Tropix Luciferase Assay Kit (Applied Biosystems, Bedford, USA, Cat No. BC100L). The production of human placental secreted alkaline phosphatase (SEAP) was quantified with the p-nitrophenylphosphate-based light absorbance time course method as described previously [Berger J, Hauber J, Hauber R, Geiger R, Cullen B R, Gene 1988; 66:1-10; Schlatter S, Rimann M, Kelm J, Fussenegger M, Gene 2002; 282:19-31]. Enhanced YFP-expression was detected by fluorescence microscopy (Leica Microsystems, Wetzlar, Germany)

Western Blot Analysis

The immunohistochemical detection of HA-tagged secreted cellulase was performed from cell culture supernatant of $4\times10^4$ CK04 cells that were transiently transfected for LHR-signaling dependent cellulase expression (pCK71, $P_{CRE}$-cellulase-pA). 48 h post-transfection 200 µl of cell culture supernatants were denatured with 50 µl of 5×SDS-PAGE reducing sample buffer (250 mM Tris, 10% sodium dodecylsulfate, 50% glycerol, 500 mM dithiothreitol, 0.01% bromphenolblue, pH 6.8) at 95° C. for 5 min. The proteins were separated by size on a 10% SDS-polyacrylamide gel and transferred to a polyvinylidene fluoride membrane (Millipore Corporation, Bedford, USA, Cat. No. IPVH20200). Unspecific binding sites were blocked with 5% (w/v) low fat milk (Migros, Switzerland) in Tris-buffered saline (TBS, 20 mM Tris, 150 mM NaCl, pH 7.6). Secreted cellulase was detected with a primary rabbit polyclonal anti-HA-tag antibody (Santa Cruz Biotechnology, CA, USA, Cat. No. sc-805, 1:1000 dilution in 1% (w/v) low fat milk in TBS) and visualized with a secondary horseradish peroxidase-coupled anti-rabbit IgG (MorphoSys AbD GmbH, Düsseldorf, Germany, 1:4000 dilution in 1% (w/v) low fat milk in TBS). The chemiluminescence-based signal detection (ECL plus, GE Healthcare, Piscataway, N.J., USA, Cat. No. RPN2132) was performed with a Chemilux CCD camera (Intas, Göttingen, Germany).

Test of Bovine Fucosyltransferase and Annexin 1 and 5 for Sperm Binding Capacity The transgenic expression of either bovine annexin (ANXA) 1 or 5 in the absence or presence of fucosyltransferase (Fut) resulted in a binding of sperm to the surface of transgenic cells. Either HEK293T or CHO-K1 cells were co-transfected with (i) pANXA1 ($P_{CMV}$-ANXA1-pA), (ii) pANXA5 ($P_{CMV}$-ANXA5-pA), (iii) pANXA1+pFut ($P_{CMV}$-ANXA1-pA, $P_{CMV}$-Fut-pA), or (iv) pANXA5+pFut ($P_{CMV}$-ANXA5-pA, $P_{CMV}$-Fut-pA), in a 6 well plate. 48 hours after transfection cryopreserved bull sperm were thawed (6 straws) for 30 seconds at 37° C., collected by centrifugation (2 min, 300×g, 37° C.) and resuspended in 7 mL of Dulbeccos modified Eagles Medium (DMEM) containing 10% fetal calf serum (FCS). 2 mL of the sperm solution were transferred on the transfected cells, the cells were cultured in a humidified atmosphere at 37° C. with 5% carbon dioxide and videos were recorded 15 h post-addition of sperm. We could show that all cells transfected with ANXA1 or 5 in the absence or presence of fucosyltransferase could bind sperm on their surface. The bound sperm created clusters and were viable and motile after 15 h. However, wild type CHO-K1 or HEK293T cells which do not express endogenous ANXA1 or 5 could not bind sperm which resulted in strongly reduced viability and no motility.

The invention claimed is:

1. A semipermeable microcapsule comprising a polymer or polymer mixture degradable by a polypeptide, wherein the microcapsule further comprises a genetically engineered cell expressing a luteinizing hormone receptor and expressing said polypeptide in response to luteinizing hormone activation of said luteinizing hormone receptor, wherein the genetically engineered cell comprises an expression vector encoding said polypeptide, the vector being operably linked to an inducible promoter responsive to a signaling compound activated by said luteinizing hormone activation of said luteinizing hormone receptor.

2. The microcapsule according to claim 1 which is non-toxic, does not elicit an immunological response and has an average half life time of at least 1 day in mammals.

3. The microcapsule according to claim 1 wherein the polymer is selected from the group consisting of oligosaccharides, oligopeptides, polyesters and polyamides, and mixtures thereof with each other and with other organic polymers.

4. The microcapsule according to claim 3 wherein the polymer is cellulose sulphate.

5. The microcapsule according to claim 3 wherein the polymer is cellulose sulfate/poly-diallyl-dimethyl-ammonium chloride.

6. The microcapsule according to claim 3 wherein the polymer is cellulose sulphate-carboxymethyl cellulose/poly-diallyl-dimethyl-ammonium chloride.

7. The microcapsule according to claim 1 which is permeable to compounds with a molecular weight below 20-50 kDA.

8. The microcapsule according to claim 1, wherein said polypeptide expressed by the genetically engineered cell is cellulase.

9. The microcapsule according to claim 1, wherein the microcapsule further comprises sperm.

10. A method of artificial insemination comprising administering to the uterus of a female prior to ovulation an effective amount of a microcapsule according to claim 9 optionally further comprising a cell expressing and secreting fucosyltransferase and/or annexin.

11. The microcapsule according to claim 1, wherein said polypeptide expressed by the genetically engineered cell is cellulase and wherein said signaling compound is cAMP.

12. The microcapsule according to claim 11 wherein the inducible promoter responsive to cAMP is CREB1.

\* \* \* \* \*

SEQUENCE LISTING

```
<160> NUMBER OF SEQ ID NOS: 8

<210> SEQ ID NO 1
<211> LENGTH: 98
<212> TYPE: DNA
<213> ORGANISM: Artificial sequence
<220> FEATURE:
<223> OTHER INFORMATION: Synthetic construct; probe for Bacillus
      subtilis 168 cellulase

<400> SEQUENCE: 1
cgggatccac catggagaca gacacactcc tgctatgggt actgctgctc tgggttccag      60
gttccactgg tgacgcaggg acaaaaacgc cagtagcc                              98

<210> SEQ ID NO 2
<211> LENGTH: 37
<212> TYPE: DNA
<213> ORGANISM: Artificial sequence
<220> FEATURE:
<223> OTHER INFORMATION: Synthetic construct; probe for Bacillus
      subtilis 168 cellulase

<400> SEQUENCE: 2
ggaattctca tctagaattt ggttctgttc cccaaat                               37

<210> SEQ ID NO 3
<211> LENGTH: 39
<212> TYPE: DNA
<213> ORGANISM: Artificial sequence
<220> FEATURE:
<223> OTHER INFORMATION: Synthetic construct; probe for CREB1 responsive
      TATA-like promoter

<400> SEQUENCE: 3
ggggtaccag gcctgagctc ttatcatgtc tggatcagc                             39

<210> SEQ ID NO 4
<211> LENGTH: 38
<212> TYPE: DNA
<213> ORGANISM: Artificial sequence
<220> FEATURE:
<223> OTHER INFORMATION: Synthetic construct; probe for CREB1 responsive
      TATA-like promoter

<400> SEQUENCE: 4
ggaattccat ggatcgatat ataccctcta gagtctcc                              38
```

```
<210> SEQ ID NO 5
<211> LENGTH: 53
<212> TYPE: DNA
<213> ORGANISM: Artificial sequence
<220> FEATURE:
<223> OTHER INFORMATION: Synthetic construct; probe for cellulase from
      pDF260

<400> SEQUENCE: 5
gactagtggg tatatagatc taagcttgaa ttccaccatg gagacagaca cac          53

<210> SEQ ID NO 6
<211> LENGTH: 62
<212> TYPE: DNA
<213> ORGANISM: Artificial sequence
<220> FEATURE:
<223> OTHER INFORMATION: Synthetic construct; probe for cellulase from
      pDF260

<400> SEQUENCE: 6
gctctagatc aagcgtaatc tggaacatcg tatgggtaat ttggttctgt tccccaaatc   60
ag                                                                 62

<210> SEQ ID NO 7
<211> LENGTH: 31
<212> TYPE: DNA
<213> ORGANISM: Artificial sequence
<220> FEATURE:
<223> OTHER INFORMATION: Synthetic construct; probe for eYFP from pDF60

<400> SEQUENCE: 7
gctctagatt acttgtacag ctcgtccatg c                                 31

<210> SEQ ID NO 8
<211> LENGTH: 34
<212> TYPE: DNA
<213> ORGANISM: Artificial sequence
<220> FEATURE:
<223> OTHER INFORMATION: Synthetic construct; probe for eYFP from pDF60

<400> SEQUENCE: 8
ggaattccaa gcttccacca tggtgagcaa gggc                              34
```